(12) United States Patent
Zacks et al.

(10) Patent No.: US 7,811,832 B2
(45) Date of Patent: Oct. 12, 2010

(54) METHODS FOR PRESERVING THE VIABILITY OF PHOTORECEPTOR CELLS BY ANTI-FAS-LIGAND/ANTI-FAS-RECEPTOR ANTIBODIES

(75) Inventors: David Zacks, Ann Arbor, MI (US); Joan W. Miller, Winchester, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 910 days.

(21) Appl. No.: 10/892,787

(22) Filed: Jul. 16, 2004

(65) Prior Publication Data

US 2005/0129684 A1 Jun. 16, 2005

Related U.S. Application Data

(63) Continuation-in-part of application No. PCT/US03/01648, filed on Jan. 17, 2003.

(60) Provisional application No. 60/349,918, filed on Jan. 18, 2002.

(51) Int. Cl.
*G01N 33/53* (2006.01)
*A61K 49/16* (2006.01)
*A61K 38/00* (2006.01)
*A61K 39/395* (2006.01)
*A61K 39/00* (2006.01)
*C12N 5/00* (2006.01)
*C12N 5/079* (2006.01)
*C12N 5/071* (2006.01)

(52) U.S. Cl. ............................ 436/547; 436/548; 514/2; 424/9.2; 424/130.1; 424/142.1; 435/368; 435/366

(58) Field of Classification Search ........................ None
See application file for complete search history.

(56) References Cited

U.S. PATENT DOCUMENTS

| 5,444,042 | A | 8/1995 | Bartus et al. |
| 5,622,967 | A | 4/1997 | Dolle et al. |
| 5,641,750 | A | 6/1997 | Louis |
| 5,667,968 | A | 9/1997 | LaVail et al. |
| 5,760,048 | A | 6/1998 | Wang et al. |
| 5,767,079 | A | 6/1998 | Glaser et al. |
| 5,840,719 | A | 11/1998 | Rubin et al. |
| 6,083,944 | A | 7/2000 | Chatterjee et al. |
| 6,100,267 | A | 8/2000 | Daines et al. |
| 6,180,402 | B1 | 1/2001 | Granville et al. |
| 6,225,303 | B1 | 5/2001 | Miller et al. |
| 6,245,523 | B1 | 6/2001 | Altieri |
| 6,303,579 | B1 | 10/2001 | Pang et al. |
| 6,316,465 | B1 | 11/2001 | Pershadsingh et al. |
| 6,331,523 | B1 | 12/2001 | Kljavin et al. |
| 6,384,073 | B1 | 5/2002 | Sakuma et al. |
| 6,397,849 | B1 | 6/2002 | Bowman et al. |
| 6,433,147 | B1 | 8/2002 | Ni et al. |
| 6,455,040 | B1 | 9/2002 | Wei et al. |
| 6,465,464 | B2 | 10/2002 | Wheeler et al. |
| 6,506,569 | B1 | 1/2003 | Ni et al. |
| 6,534,693 | B2 | 3/2003 | Fischell et al. |
| 6,623,941 | B1 | 9/2003 | Ruben et al. |
| 6,750,196 | B1 | 6/2004 | Reh et al. |
| 2001/0026801 | A1 | 10/2001 | Tobinick |
| 2002/0040015 | A1 | 4/2002 | Miller et al. |
| 2003/0008857 | A1 | 1/2003 | Hunt et al. |
| 2003/0083649 | A1 | 5/2003 | Margaron et al. |
| 2003/0104618 | A1 | 6/2003 | Hughes |
| 2004/0097425 | A1 | 5/2004 | Shima et al. |
| 2005/0129684 | A1 | 6/2005 | Zacks et al. |
| 2006/0204504 | A1 | 9/2006 | Gragoudas et al. |
| 2006/0269520 | A1 | 11/2006 | Korneluk et al. |
| 2007/0032427 | A1 | 2/2007 | Grosskreutz |
| 2007/0287756 | A1 | 12/2007 | Nakazawa |

FOREIGN PATENT DOCUMENTS

| EP | 1 717 246 | 11/2006 |
| WO | WO-95/33051 | 12/1995 |
| WO | WO-98/18485 | 5/1998 |
| WO | WO-00/38703 | 7/2000 |
| WO | WO-00/51638 | 9/2000 |
| WO | WO2000/61150 | 10/2000 |
| WO | WO-01/09327 A2 | 2/2001 |

(Continued)

OTHER PUBLICATIONS

Adida et al. (1998) "Developmentally Regulated Expression of the Novel Cancer Anti-Apoptosis Gene Survivin in Human and Mouse Differentiation," Am. J. Pathol. 152(1): 43-49.

Afford et al. (2000) "Demystified . . . Apoptosis," J. Clin. Pathol. 53: 55-63.

Ambrosini et al. (1997) "A novel anti-apoptosis gene, survivin, expressed in cancer and lymphoma," Nat. Med. 3(8): 917-21.

Ambrosini et al. (1998) "Induction of Apoptosis and Inhibition of Cell Proliferation by survivin Gene Targeting," J. Biol. Chemistry 273(18): 11177-82.

Anderson et al. (1983) "Retinal Detachment in the Cat: The Pigment Epithelial-Photoreceptor Interface," Invest. Ophthalmol. Vis. Sci. 24: 906-926.

(Continued)

*Primary Examiner*—Christine J Saoud
*Assistant Examiner*—Chang-Yu Wang
(74) *Attorney, Agent, or Firm*—Goodwin Procter LLP

(57) ABSTRACT

Provided are methods and compositions for maintaining the viability of photoreceptor cells following retinal detachment. The viability of photoreceptor cells can be preserved by administering an apoptosis inhibitor to a mammal having an eye with retinal detachment. The apoptosis inhibitor maintains the viability of the photoreceptor cells until such time that the retina becomes reattached to the underlying retinal pigment epithelium and choroid. The treatment minimizes the loss of vision, which otherwise may occur as a result of retinal detachment.

10 Claims, 6 Drawing Sheets

FOREIGN PATENT DOCUMENTS

| WO | WO-01/49321 | 7/2001 |
|---|---|---|
| WO | WO-03/061519 | 7/2003 |
| WO | WO-2005/105133 | 11/2005 |
| WO | WO-2006/051638 | 5/2006 |
| WO | WO-2006/091666 | 8/2006 |
| WO | WO-2007/019427 | 2/2007 |
| WO | WO-2008/063639 | 5/2008 |

OTHER PUBLICATIONS

Anderson et al. (1986) "Morphological Recovery in the Reattached Retina," Invest. Ophthalmol. Vis. Sci. 27: 168-83.

Angelastro et al. (2001) "Characterization of a novel isoform of caspase-9 that inhibits apoptosis," J. Biol. Chem. 276(15): 12190-200.

Antonsson et al. (2000)"The Bcl-2 Protein Family," Experiment. Cell Res. 256: 50-57.

Asai et al (1999) "High level calcineurin activity predisposes neuronal cells to apoptosis," J Biol Chem 274(48):34450-8.

Bamford et al. (2000) "Therapeutic Applications of Apoptosis Research," Experimental Cell Res. 256: 1-11.

Berglin et al. (1997) Photoreceptor decay over time and apoptosis in experimental retinal detachment, Graefs Arch. Clin. Exp. Ophthalmol. 235:306-12.

Bratton et al. (2000) "Protein Complexes Activate Distinct Caspase Cascades in Death Receptor and Stress-Induced Apoptosis," Experim. Cell Res. 256: 27-33.

Burton (1982) "Recovery of Visual Acuity After Retinal Detachment Involving The Macula," Tr. Am. Ophth. Soc. LXXX: 475-497.

Calbiochem Catalog (1999), (4 pages).

Cao et al. (2001) "Intracellular Bax translocation after transient cerebral ischemia: Implications for a role of the mitochondrial apoptotic signaling pathway in ischemic neuronal death," J. Cer. Blood Flow Met. 21: 321-33.

Caspase-Inhibitors, from http://www.celldeath.de/encyclo/caspases/inhibito.htm, viewed Jan. 13, 2003 (2 pages).

Chang et al. (1995) "Apoptotic Photoreceptor Cell Death After Traumatic Retinal Detachment in Humans," Arch Ophthalmol. 113: 880-886.

Chen et al. (1996) "bcl-2 overexpression reduces apoptotic photoreceptor cell death in three different retinal degenerations," Proc Natl Acad Sci USA 93(14):7042-7.

Cleary et al. (1977) "Macular Morphology in the Re-Attached Retina," Mod. Probl. Ophthal. 18: 400-407.

Cook et al. (1995) "Apoptotic Photoreceptor Degeneration in Experimental Retinal Detachment," Invest. Ophthalmol. Vis. Sci. 36(6): 990-96.

Cross et al.(2000) "Serine/Threonine Protein Kinases and Apoptosis," Experiment. Cell Res. 256: 34-41.

Deveraux et al. (1997) "X-linked IAP is a direct inhibitor of cell-death proteases," Nature 388(6639): 300-04.

Deveraux et al. (1998) "IAPs block apoptotic events induced by caspase-8 and cytochrome c by direct inhibition of distinct caspases.," EMBO Journal 17(8): 2215-23.

Donovan et al. (2001) "Light-induced photoreceptor apoptosis in vivo requires neuronal nitric-oxide synthase and guanylate cyclase activity and is caspase-3-independent," J. Biol. Chem. 276:23000-8.

Dunaief et al. (2002) "The role of apoptosis in age-related macular degeneration," Arch. Ophthalmol. 120: 1435-42.

Ekert et al. (1999) "Review: Caspase Inhibitors," Cell Death and Differentiation 6: 1081-1086.

Erickson et al. (1983) "Retinal Detachment in the Cat: The Outer Nuclear and Outer Plexiform Layers," Invest. Ophthalmol. Vis, Sci.: 927-942.

Faktorovich et al. (1990) "Photoreceptor degeneration in inherited retinal dystrophy delayed by basic fibroblast growth factor," Nature 347(6288):83-6.

Fisher et al. (1991) "Retinal Proliferation Induced by Retinal Detachment," Invest. Ophthalmol. Vis. Sci. 32(6): 1739-48.

Gregory et al. (1995) "Cell loss in retinal dystrophies by apoptosis—death by informed consent!," Brit. J. Ophthalmol. 79: 186-190.

Grimm et al. (2000) "Gene expression in the mouse retina: The effect of damaging light," Molecular Vision 6: 252-60.

Guerin et al. (1989) "Retinal Reattachment of the Primate Macula," Invest. Ophthalmol. Vis. Sci. 30(8): 1708-1724.

Guerin et al. (1993) "Recovery of Photoreceptor Outer Segment Length and Analysis of Membrane Assembly Rates in Regenerating Primate Photoreceptor Outer Segments," Invest. Ophthalmol. Vis. Sci. 34(1): 175-83.

Hafezi et al. (1997) "The absence of c-fos prevents light-induced apoptotic cell death of photoreceptors in retinal degeneration in vivo," Nat Med 3(3):346-9.

Hagimura et al. (2002) "Persistent Foveal Retinal Detachment After Successful Rhegmatogenous Retinal Detachment Surgery," Amer. J. Ophthalmol. 133(4): 516-520.

Hakem et al. (1998) "Differential requirement for caspase 9 in apoptotic pathways in vivo," Cell 94:339-352.

Harada et al. (2000) "N-acetylated-alpha-linked-acidic dipeptidase inhibitor has a neuroprotective effect on mouse retinal ganglion cells after pressure-induced ischemia," Neur. Lett. 292:134-36.

Harrison et al. (2001) "Caspase mRNA expression in a rat model of focal cerebral ischemia," Mol. Brain. Res. 89: 133-46.

He et al. (2000) "Lead and Calcium Produce Rod Photoreceptor Cell Apoptosis by Opening the Mitochondrial Permeability Transition Pore," J. of Biol. Chem. 275(16): 12175-12184.

Hengartner (2000) "The biochemistry of apoptosis," Nature 407: 770-.

Hisatomi et al. (2001) "Relocalization of Apoptosis-Inducing Factor in Photoreceptor Apoptosis Induced by Retinal Detachment in Vivo," Am. J. of Pathol. 158(4):1271-78.

Hisatomi et al. (2002) "Critical Role of photoreceptor apoptosis in functional damage after retinal detachment," Curr. Eye Res. 24(3): 161-172.

Hobson et al. (2000) "Apoptotic Photoreceptor Death in the Rhodopsin Knockout Mouse in the Presence and Absence of c-fos," Exp. Eye Res. 71: 247-254.

Hockenberry et al. (1993) "Bcl-2 functions in an antioxidant pathway to prevent apoptosis," Cell 75:241-251.

Honjo et al. (2000) "Expression of Ciliary Neurotrophic Factor Activated by Retinal Muller Cells in Eyes with NMDA- and Kainic Acid-Induced Neuronal Death," Invest. Ophthalmol. Vis. Sci. 41(2): 552-59.

Huppertz et al. (1999) "The apoptosis cascade—morphological and immunohistochemical methods for its visualization," Anat. Embryol. 200:1-8.

International Search Report for Application No. PCT/US03/01648 dated Jul. 7, 2004 (2 pages).

Johnson et al. (2003) "Drusen-associated degeneration in the retina," Invest. Ophthalmol. Vis. Sci. 44: 4481-88.

Jomary et al. (2001) "Characterization of Cell Death Pathways in Murine Retinal Neurodegeneration Implicates Cytochrome c Release, Caspase Activation, and Bid Cleavage," Molec. Cell. Neurosci. 18: 335-46.

Kane et al. (1993) "Bcl-2 inhibition of neural death: decreased generation of reactive oxygen species." Science 262:1274-1277.

Kantrow et al. (2000) "Regulation of tumor necrosis factor cytotoxicity by calcineurin." FEBS Lett 483(2-3):119-24.

Kapin et al. (1999) "Neuroprotective Effects of Eliprodil in Retinal Excitotoxicity and Ischemia," Invest. Ophthalmol. Vis. Sci. 40(6): 1177-82.

Katai et al. (1999) "Caspaselike Proteases Activated in Apoptotic Photoreceptors of Royal College of Surgeon Rats," Invest. Ophthalmol. Vis. Sci. 40(8): 1802-07.

Kaufman et al. (1999) "Introductory Comments on Neuroprotection," Survey Ophthalmol. 43(1): S89-90.

Kaufman et al. (2000) "Induction of Apoptosis by Cancer Chemotherapy," Experiment. Cell Res. 256, 42-49.

Kerr et al. (1972) "Apoptosis: a basic biological phenomenon with wide-ranging implications in tissue kinetics," Br. J. Cancer 26:239-257.

Koike (1992) "Molecular and cellular mechanism of neuronal degeneration caused by nerve growth factor deprivation approached through PC12 cell culture," Neuro-Psychopharmacol. Biol. Psychiat. 16:95-106.

Kreissig (1977) "Prognosis of Return of Macular Function after Retinal Reattachment," Mod. Probl. Ophthal. 18: 415-429.

Kroemer et at (1997) "The proto-oncogene Bcl-2 and its role in regulating apoptosis," Nat. Med. 3:614-620.

Krupinski et al. (2000) "Expression of caspases and their substrates in the rat model of focal cerebral ischemia," Neurobiol. Dis. 7: 332-42.

Kusaka et al. (1998) "Long-Term Visual Recovery After Scleral Buckling for Macula-off Retinal Detachments," Jpn. J. Ophthalmol. 42: 218-222.

Kwong et al. (2000) "N-Methyl-D-Aspartate (NMDA) Induced Apoptosis in Adult Rabbit Retinas," Exp. Eye Res. 71: 437-44.

LaCasse et al. (1998) "The inhibitors of apoptosis (IAPs) and their emerging role in cancer," Oncogene 17: 3247-59.

LaVail et al. (1998) "Protection of Mouse Photoreceptors by Survival Factors in Retinal Degenerations," Invest. Ophthalmol. Vis. Sci. 39(3): 592-602.

Lewis et al. (1995) "Changes in the Organization and Expression of Cytoskeletal Proteins During Retinal Degeneration Induced by Retinal Detachment," Invest. Ophthalmol. Vis. Sci. 36(12): 2404-16.

Lewis et al. (1998) "Neurite Outgrowth from Bipolar and Horizontal Cells after Experimental Retinal Detachment," Invest. Ophthalmol. Vis. Sci. 39(2): 424-34.

Lewis et al. (1999) "Effects of the Neurotrophin Brain-Derived Neurotrophic Factor in an Experimental Model of Retinal Detachment" Invest. Ophthalmol. Vis. Sci. 40(7): 1530-44.

Lewis et al. (1999) "Limiting the proliferation and reactivity of retinal Müller cells during experimental retinal detachment: the value of oxygen supplementation," Am. J. Ophthalmol. 128:165-172.

Lin et al. (1999) "Ischemic Preconditioning Attenuates Hypoperfusion after Retinal Ischemia in Rats," Invest. Ophthalmol. Vis. Sci. 40(12): 2925-31.

Lipton et al. (2002) "Dueling activities of AIF in cell death versus survival: DNA binding and redox activity," Cell 111: 147-50.

Liu et al. (1999) "Activation of Caspase-3 in the Retina of Transgenic Rats with the Rhodopsin Mutation S334ter during Photoceptor Degeneration," Jour. Neurosci. 19(12): 4778-4785.

Loeffler et al. (2000) "The Mitochondrion in Cell Death Control: Certainties and Incognita," Exp. Cell Res. 256: 19-26.

Lolley (1994) "The rd Gene Defect Triggers Programmed Rod Cell Death," Invest. Ophthalmol. Vis. Sci. 35(13): 4182-91.

Love (2003) "Apoptosis and brain ischaemia," Prog. Neuropsychopharm Biol. Psych. 27: 267-82.

Lu et al. (2000) "Advances in Secondary Spinal Cord Injury," Spine 25(14) 1859-66.

Luthert et al. (1998) "Photoreceptor rescue," Eye 12: 591-96.

Marc et al. (1998) "Amino Acid Signatures in the Detached Cat Retina," Invest. Ophthalmol. Vis. Sci. 39(9): 1694-702.

Martin et al. (1992) "Biochemical characterization of programmed cell death in NGF-deprived sympathetic neurons," J. Neurobiol. 23:1205-1220.

Mervin et al. (1999) "Limiting photoreceptor death and deconstruction during experimental retinal detachment: The value of oxygen supplementation," Am. J. Ophthalmol. 128(2): 155-64.

Moore et al. (1993) "Noninvasive measurement of rat intraocular pressure with the Tono-pen." Invest. Ophthalmol. Vis. Sci. 34: 363-69.

Nakajima et al. (1996) "Photoreceptor Apoptosis Induced by a Single Systemic Administration of N-Methyl-N-Nitrosourea in the Rat Retina," Amer. Jour. Pathol. 148(2): 631-41.

Nickells et al. (1996) "Apoptosis in ocular disease: a molecular overview," Ophthalmic Genetics 17(4): 145-65.

Nir et al. (2000) "Expression of Bcl-2 protects against photoreceptor degeneration in retinal degeneration in slow (rds) mice," J Neurosci 20(6):2150-4.

Oppenheim (1991) "Cell death during development of the nervous system," Ann. Rev. Neurosci. 14:453-501.

Ozaki et al. (2000) "Rapid upregulation of fibroblast growth factor receptor 1 (flg) in rat photoreceptor cells after injury," Invest. Ophthalmol. Vis. Sci. 41(2): 568-79.

Papapetropoulos et al. (2000) "Angiopoietin-1 inhibits endothelial cell apoptosis via the Akt/survivin pathway," Biol. Chem. 275:9102-9105.

Poon et al. (2000) "c-Fos Protein in Photoreceptor Cell Death after Photic Injury in Rats," Invest. Ophthalmol. Vis. Sci. 41(9): 2755-.

Ranger et al. (2001) "Mouse models of cell death," Nature Genetics 28: 113-18.

Reme et al. (1998) "Apoptotic Cell Death in Retinal Degenerations," Progress Retinal Eye Res. 17 (4): 443-64.

Rosenbaum et al. (2000) "Fas (CD95/APO-1) plays a role in a pathophysiology of focal cerebral ischemia," J. Neurosci. Res. 61: 686-92.

Ross et al. (1998) "Visual Recovery in Macula-off Rhegmatogenous Retinal Detachments," Ophthalmology 105(11): 2149-53.

Ross et al. (2000) "Visual recovery after retinal detachment," Curr. Opinion Ophthalmol. 11: 191-194.

Roy et al. (1997) "Soluble factor(s) produced by adult bone marrow stroma inhibit in vitro proliferation and differentiation of fetal liver BFU-E by inducing apoptosis," J. Clin. Invest. 100(4): 912-20.

Rydel (1988) "cAMP analogs promote survival and neurite outgrowth in cultures of rat sympathetic and sensory neurons independently of nerve growth factor," Proc. Nat. Acad. Sci. USA 85:1257-1261.

Sasoh et al. (1998) "Immunocytochemical localization of glutamate in normal and detached cat retina," Invest Ophthalmol Vis Sci 39(5):786-92.

Sebang (1996) "Apoptotic Photoreceptor Cell Death After Traumatic Retinal Detachment in Humans," Invest. Ophthalmol. Vis. Sci. 114: 1158.

Sherry et al. (2000) "Rapid Glutamatergic Alterations in the Neural Retina Induced by Retinal Detachment," Invest. Ophthalmol. Vis. Sci. 41(9): 2779-90.

Singh et al. (2001) "Cell-specific caspase expression by different neuronal phenotypes in transient retinal ischemia," J. Neurochem. 77: 466-475.

Sintzel et al. (1996) "Biomaterials in Ophthalmic Drug Delivery," Eur. J. Pharm. Biopharm. 42: 358-372.

Solberg et al. (1997) "MK-801 Has Neuroprotective and Antiproliferative Effects in Retinal Laser Injury," Invest. Ophthalmol. Vis. Sci. 38(7): 1380-89.

Susin et al. (1999) "Molecular characterization of mitochondrial apoptosis-inducing factor," Nature 397: 441-46.

Tamm et al. (1998) "IAP-family protein survivin inhibits caspase activity and apoptosis induced by Fas (CD95), Bax, caspases, and anticancer drugs," Cancer Res. 58: 5315-20.

Theodosiadis et al. (1994) "Experimental Transient Exudative Retinal Detachment in the Rat," Arch Ophthalmol. 112: 1236-1242.

Veis et al. (1993) "Bcl-2-deficient mice demonstrate fulminant lymphoid apoptosis, polycystic kidneys, and hypopigmented hair," Cell 75:229-240.

Virgili et al. (1998) "Bcl-2 overexpression in the HaCaT cell line is associated with a different membrane fatty acid composition and sensitivity to oxidative stress," Free Radicals Biol. Med. 24:93-101.

Walczak et al. (2000) "The CD95 (APO-1/Fas) and the TRAIL (APO-2L) Apoptosis Systems," Exp. Cell Res. 256: 58-66.

Walker et al. (1988) "Patterns of cell death," Meth. Achie. Exp. Pathol. 13:18-54.

Wang et al. (2002) "Mechanisms of AIF-mediated apoptotic DNA degradation in *Caenorhabditis elegans*," Science 298: 1587-92.

Weise et al. (2001) "Increased expression and activation of poly(ADP-ribose) polymerase (PARP) contribute to retinal ganglion cell death following rat optic nerve transection," Cell Death and Differentiation 8: 801-07.

Wenzel et al. (2001) "Prevention of photoreceptor apoptosis by activation of the glucocorticoid receptor," Invest. Ophthamol. Vis. Sci. 42(7): 1653-59.

Wilson et al. (1987) "Histopathologic Study of the Effect of Retinal Detachment Surgery on 49 Eyes Obtained Post Mortem," Amer. Jour. Ophthalmol. 103:167-179.

Wilson et al. (1995) "Apoptosis as the Mechanism of Photoreceptor Cell Death in Experimental Retinal Detachment," Invest. Ophthamol. Vis. Sci. 36(4) Abstract of Poster Presentation #308-216.

Wu et al. (2002) "Gene therapy for detached retina by adeno-associated virus vector expressing glial cell line-derived neurotrophic factor," Invest. Ophthamol. Vis. Sci. 43(11): 3480-88.

Wyllie et al. (1980) "Cell death: the significance of apoptosis," Int. Rev. Cytology 68:251-306.

Ge-Zhi et al. (1996) "Apoptosis in Human Retinal Degenerations," Tr. Am. Ophth. Soc. XCIV: 411-431.

Yang et al. (Feb. 2004) "Preventing Retinal Detachment-Associated Photoreceptor Cell Loss in Bax-Deficient Mice," Invest. Ophthalmol. .Vis. Sci. 45(2): 648-54.

Yoshizawa et al. (2000) "Caspase-3 Inhibitor Rescues N-Methyl-N-nitrosourea-induced Retinal Degeneration in Sprague-Dawley Rats," Exp. Eye Res. 71: 629-35.

Yuan et al. (2002) "Apoptosis in the nervous system," Nature 407(12): 802-809.

Zacks et al. (Mar. 2003) Caspase Activation in an Experimental Model of Retinal Detachment, Investigative Ophthalmology & Visual Science 44(3): 1262-67.

Zheng et al. (2000) "Divinations and Surprises: Genetic Analysis of Caspase Function in Mice," Experiment. Cell Res. 256: 67-73.

Zhu et al. (2000) "Stabilization of proteins encapsulated in injectable poly (lactide-co-glycolide)," Nat. Biotechnol. 18: 52-.

Aaberg (1999) "Does hyperoxygenation limit retinal degeneration after retinal detachment?" Am J Ophthalmol. 128(2):231.

Ahmed et al. (2004), Microarray analysis of changes in mRNA levels in the rat retina after experimental elevation of intraocular pressure. Invest Ophthalmol Vis Sci, 45: 1247-58.

Aiello, (1994), "Vascular endothelial growth factor in ocular fluid of patients with diabetic retinopathy and other retinal disorders", Surv Ophthalmol, 331(22):1480-7.

Almeida et al. (2004) "FK506 prevents mitochondrial-dependent apoptotic cell death induced by 3-nitropropionic acid in rat primary cortical cultures," Neurobiol Dis. 17: 435-444.

Ambati et al. (1997) "Elevated gamma-aminobutyric acid, glutamate, and vascular endothelial growth factor levels in the vitreous of patients with proliferative diabetic retinopathy," Arch. Ophthalmol. 115(9): 1161-1166.

Ament et al. (2002) "Traumatic Choroidal Rupture: Visual Outcome and Treatment of Choroidalneovascular Membranes," Invest. Ophthalmol. Vis. Sci. 43: E-Abstract 4491.

Bavetta et al. (1999) "The effects of FK506 on dorsal column axons following spinal cord injury in adult rats: neuroprotection and local regeneration," Exp Neurol. 158: 382-393.

Bochelen et al. (1999) "Calcineurin inhibitors FK506 and SDZ ASM 981 alleviate the outcome of focal cerebral ischemic/reperfusion injury," J Pharmacol Exp Ther. 288: 653-659.

Brooks et al. (1997) "Vitreous body glutamate concentration in dogs with glaucoma," Am. J. Vet. Res. 58(8): 864-867.

Bryckaert et al. (1999) "Both FGF1 and Bcl-x synthesis are necessary for the reduction of apoptosis in retinal pigmented epithelial cells by FGF2: role of the extracellular signal-regulated kinase 2," Oncogene 18(52): 7584-7593.

Bula et al. (2004) "Pigment Epithelium-derived Factor, Angiopoietin-1 and VEGF Expression in human Choroidal Neovascular Membranes treated with Photodynamic Therapy," Invest. Ophthalmol. Vis. Sci. 45: E-Abstract 1787.

Butcher et al. (1997) "Neuroprotective actions of FK506 in experimental stroke: in vivo evidence against an antiexcitotoxic mechanism," J Neurosci. 17: 6939-6946.

Caffe et al. (2001) "A Combination of CNTF and BDNF Rescues rd Photoreceptors but Changes Rod Differentiation in the Presence of RPE in Retinal Explants," Invest. Ophthalmol. Vis. Sci. 42:275-282.

Campbell et al. (1999) "Spontaneous axonal regeneration after optic nerve injury in adult rat," Neuroreport 10(18): 3955-60.

Cao et al. (1999) "Pigment epithelium-derived factor protects cultured retinal neurons against hydrogen peroxide-induced cell death," J Neurosci Res. 57: 789-900.

Capeans et al. (1998) "C-C chemokines in the vitreous of patients with proliferative vitreoretinopathy and proliferative diabetic retinopathy," Retina 18(6): 546-550.

Cayouette et al. (1999) "Pigment epithelium-derived factor delays the death of photoreceptors in mouse models of inherited retinal degenerations," Neurobiol Dis. 6(6):523-32.

Chatterjee et al. (1997) "Synthesis and Biological Activity of a Series of Potent Fluoromethyl Ketone Inhibitors of Recombinant Human Calpain I," J Med Chem. 40: 3820-3838.

Chen et al. (1998) "Relationship between IL-1 beta and TNF-alpha in subretinal fluids of rhegmatogenous retinal detachment with PVR," Hunan Yi Ke Da Xue Xue Bao. 23(5): 483-485.

Cheng et al. (1998) "Caspase Inhibitor Affords Neuroprotection with delayed administration in a rat model of neonatal hypoxic-ischemic brain injury," J Clin Invest. 101:, 1992-1999.

Coleman et al. (2005) "Axon degeneration mechanisms: commonality amid diversity," Nat Rev Neurosci. 6: 889-98.

Cuthbertson RA, Lang RA, Coghlan JP. Macrophage products IL-1 alpha, TNF alpha and bFGF may mediate multiple cytopathic effects in the developing eyes of GM-CSF transgenic mice. Exp Eye Res. (1990) vol. 51(3):335-344.

Delgado et al. (2001) "Vasoactive intestinal peptide and pituitary adenylate cyclase-activating polypeptide inhibit expression of Fas ligand in activated T lymphocytes by regulating c-Myc, NF-kappa B, NF-AT, and early growth factors 2/3," J Immunol. 166(2):1028-40.

Dockrell (2003) "The multiple roles of Fas ligand in the pathogenesis of infectious diseases," Clin Microbiol Infect. 9(8): 766-79.

Dreyer et al. (1996) "Elevated glutamate levels in the vitreous body of humans and monkeys with glaucoma," Arch. Ophthalmol. 114(3): 299-305.

Dumont (2000) "FK506, an immunosuppressant targeting calcineurin function," Curr Med Chem. 7: 731-748.

El-Ghrably IA, Dua HS, Orr GM, Fischer D, Tighe PJ. Intravitreal invading cells contribute to vitreal cytokine milieu in proliferative vitreoretinopathy. Br J Ophthalmol. (2001) vol. 85(4):461-470.

Endres et al. (1998) J Cereb Blood Flow Metab. 18:, 238-247.

Esson (2004) "Microarray analysis of the failure of filtering blebs in a rat model of glaucoma filtering surgery," Invest Ophthalmol Vis Sci. 45(12):4450-62.

Farkas et al. (2001) "Apoptosis, neuroprotection, and retinal ganglion cell death: an overview," Int. Opthalmol. Clinic. 41(1): 111-130.

Franks WA, Limb GA, Stanford MR, Ogilvie J, Wolstencroft RA, Chignell AH, Dumonde DC. Cytokines in human intraocular inflammation. Curr Eye Res. (1992) vol. 11 Suppl:187-191.

Freeman et al. (2000) "The effects of FK506 on retinal ganglion cells after optic nerve crush," Invest Ophthalmol Vis Sci. 41: 1111-15.

Garcia-Valenzuela et al. (1995) "Programmed cell death of retinal ganglion cells during experimental glaucoma," Exp Eye Res. 61:, 33-44.

Geller SF, Lewis GP, Fisher SK. FGFR1, signaling, and AP-1 expression after retinal detachment: reactive Müller and RPE cells. Invest Ophthalmol Vis Sci. (2001) vol. 42(6):1363-1369.

Grant application, grant K08-EY-14705 awarded by the National Eye Institute, funded Sep. 1, 2002.

Granville et al. (2001) "Fas ligand and TRAIL augment the effect of photodynamic therapy on the induction of apoptosis in JURKAT cells," Int Immunopharmacol. 1(9-10):1831-40.

Grosskreutz et al. (2005) "FK506 blocks activation of the intrinsic caspase cascade after optic nerve crush," Exp Eye Res. 80(5):681-86.

Grosskreutz et al. (2004), Calcineurin Activation in Experimental Glaucoma in the Rat, Invest Ophthalmol Vis Sci. 45: E-Abstract 2150-B961.

Guo et al. (2003) "Cyclophilin ligands protect against light-induced retinal degeneration in mice." Society for NeuroScience Abstract Viewer and Itinerary Planner: Abstract No. 816.8.

Guo et al. (2006) "Assessment of neuroprotective effects of glutamate modulation on glaucoma-related retinal ganglion cell apoptosis in vivo," Invest Ophthalmol Vis Sci. 47:626-33.

Hanninen et al. (2002) "Activation of caspase 9 in a rat model of experimental glaucoma," Curr Eye Res. 25:, 389-395.

Harriman et al. (2000) "Efficacy of Novel Calpain inhibitors in preventing Renal Cell death," J Pharmacol Exper Therapeut. 294(3):1083-1087.

Harriman et al. (2002) "Endoplasmic reticulum Ca2+signaling and calpains mediate renal cell death," Cell Death Different. 9:734-741.

Herr et al. (1999) "FK506 prevents stroke-induced generation of ceramide and apoptosis signaling," Brain Res. 826:, 210-219.

Hisatomi et al. (2003) "Clearance of apoptotic photoreceptors: elimination of apoptotic debris into the subretinal space and macrophage-mediated phagocytosis via phosphatidylserine receptor and integrin alphavbeta3," Amer. J. Pathol. 162(6): 1869-1879.

Huang et al. (2005) "Calcineurin Cleavage Is Triggered by Elevated Intraocular Pressure And Calcineurin Inhibition Blocks Retinal Ganglion Cell Death In Experimental Glaucoma" Proc Natl Acad Sci USA 102(34):12242-47.

Huang et al. (2005) "Neuroprotection From Calcineurin-Mediated Retinal Ganglion Cell Apoptosis by FK506 in Experimental Glaucoma," Invest. Ophthalmol. Vis. Sci. 46: E-Abstract 4726.

Huang et al. (2005) "Transcriptional up-regulation and activation of initiating caspases in experimental glaucoma," Amer J Pathol. 167(3): 673-81.

Huang et al. (2006) "Calcineurin cleavage is mediated by calpain in experimental glaucoma: a proteomic analysis," Invest Ophthalmol Vis Sci. 47: E-Abstract 196.

International Search Report for Application No. PCT/US06/006272 dated Nov. 28, 2006 (6 pages).

International Search Report for International Application No. PCT/US2005/013710, mailed on Dec 23, 2005.

International Search Report for international application PCT/US2006/030688, mailed on Mar. 13, 2007 (8 pages).

Ishida (2003) "Leukocytes mediate retinal vascular remodeling during development and vaso-obliteration in disease," Nat Med. 9(6):781-88.

Jayanthi et al. (2005) "Calcineurin/NFAT-induced up-regulation of the FAS ligand / FAS death pathway is involved in methamphetamine-induced neuronal apoptosis," Proc. Natl. Acad. Sci. USA 102: 868-873.

Jiang et al. (1999) "Selective depletion of a thymocyte subset in vitro with an immunomodulatory photosensitizer," Clin Immunol. 91(2):178-87.

Joussen et al. (2003) "Suppression of Fas-FasL-induced endothelial cell apoptosis prevents diabetic blood-retinal barrier breakdown in a model of streptozotocin-induced diabetes," FASEB J. 17(1):76-8.

Kaminska et al. (2004) "Molecular Mechanisms of Neuroprotective Action of Immunosuppressants facts and Hypotheses," J Cell Mol Med. 8(1) 45-58.

Kaplan et al. (1999) "Fas ligand (CD95 ligand) controls angiogenesis beneath the retina," Nat. Med. 5: 292-297.

Kerrigan et al. (1997) Arch. Ophthalmol. 115:, 1031-1035.

Kikuchi et al. (1998) "Protective effects of FK506 against glutamate-induced neurotoxicity in retinal cell culture," Invest Ophthalmol Vis Sci. 39(7):1227-32.

Klettner et al. (2003) "FK506 and its analogs—therapeutic potential for neurological disorders," Curr. Drug Targets CNS Neurol. Disord. 2: 153-162.

Klettner et al. (2003) "The immunophilin-ligands FK506 and V-10,367 mediate neuroprotection by the heat shock shock response," Br J Pharmacol. 138: 1004-1012.

Kroemer et al. (1995) "The biochemistry of programmed cell death," FASEB J. 9(13): 1277-1287.

Kroemer et al. (1997) "Mitochondrial control of apoptosis," Immunol. Today 18: 44-51.

Ku et al. (1995) "Regulation of basic fibroblast growth factor (bFGF) gene and protein expression following its release from sublethally injured endothelial cells," J Cell Biochem. 58(3): 328-43.

La Heij EC, Van De Waarenburg MP, Blaauwgeers HG, Kessels AG, De Vente J, Liem AT, Steinbusch H, Hendrikse F. Levels of basic fibroblast growth factor, glutamine synthetase, and interleukin-6 in subretinal fluid from patients with retinal detachment. Am J Ophthalmol. (2001) vol. 132(4):544-550.

La Heij et al. (2002) "Basic fibroblast growth factor, glutamine synthetase, and interleukin-6 in vitreous fluid from eyes with retinal detachment complicated by proliferative vitreoretinopathy," Am J Ophthalmol. 134(3):367-375.

Lang-Lazdunski et al. (2001) "The effects of FK506 on neurologic and histopathologic outcome after transient spinal cord ischemia induced by aortic cross-clamping in rats," Anesth Analg. 92: 1237-1244.

LaVail et al. (2001) "Legacy of the RCS rat: impact of a seminal study on retinal cell biology and retinal degenerative diseases," Prog. Brain Res. 131: 617-627.

Levi et al. (2004) "A review of neuroprotective agents," Curr Med Chem. 11(18): 2383-97.

Levin (1999) "Direct and indirect approaches to neuroprotective therapy of glaucomatous optic neuropathy," Survey Opthalmol. 43(Suppl.): S98-101.

Li et al. (1993) "Peptide alpha-Keto Ester, alpha-Keto Amide, and alpha-Keto Acid Inhibitors of Calpains and Other Cysteine Proteases," J. Med. Chem. 36(22): 3472-80.

Li et al. (1996) "Novel Peptidyl alpha-Keto Amide Inhibitors of Calpains and Other Cysteine Proteases," J. Med. Chem. 39(20) 4089-98.

Limb GA, Hollifield RD, Webster L, Charteris DG, Chignell AH. Soluble TNF receptors in vitreoretinal proliferative disease. Invest Ophthalmol Vis Sci. (2001) vol. 42(7):1586-1591.

Limb GA, Little BC, Meager A, Ogilvie JA, Wolstencroft RA, Franks WA, Chignell AH, Dumonde DC. Cytokines in proliferative vitreoretinopathy. Eye. 1991;5 ( Pt 6):686-693.

Lipton et al. (1994) "Excitatory Amino Acids as a Final Common Pathway for Neurologic Disorders," N. Engl. J. Med. 330(9): 613-622.

Liu et al. (2001) "Calpains mediate acute renal cell death: role of autolysis and translocation," Am. J. Physiol. Renal Physiol. 281:728-738.

Liu et al. (2002) "Cryoprotective Properties of Novel Nonpeptide Calpain Inhibitors in Renal Cells," J Pharmacol Exper Therapeut. 302(1): 88-94.

Liu et al. (2004) "The role of Calpain in Oncotic Cell Death," 44: 349-70.

Maeda et al. (2004) "A novel neuroprotectant against retinal ganglion cell damage in a glaucoma model and an optic nerve crush model in the rat," Invest Ophthalmol Vis Sci. 45: 851-56.

Martin-Villalba et al. (2001) "Therapeutic neutralization of CD95-ligand and TNF attenuates brain damage in stroke," Cell Death Differ. 8(7):679-86.

McKinnon et al. (2002) "Baculoviral IAP repeat-containing-4 protects optic nerve axons in a rat glaucoma model," Mol. Ther. 5: 780-787.

McKinnon et al. (2002) "Caspase activation and amyloid precursor protein cleavage in rat ocular hypertension," Invest Ophthalmol Visual Sci. 43: 1077-1087.

Mehendale et al. (2005) "Calpain: a death protein that mediates progression of liver injury," Trends in Pharmacol Sci. 26(5): 232-36.

Miyazawa et al. (2000) "Protective effect of FK506 in the reperfusion model after short-term occlusion of the middle cerebral artery in the rat: assessment by autoradiography using [1251]PK-11195," Neurol. Res. 22:, 630-633.

Mukerjee et al. (2000) Caspase-mediated proteolytic activation of calcineurin in thapsigargin-mediated apoptosis in SH-SY5Y neuroblastoma cells. Arch Biochem Biophys, 2000. 379(2): p. 337-43.

Nagata et al. (1994) "Fas and Fas ligand: a death factor and its receptor," Adv Immunol. 57: 129-44.

Nakazawa et al. (2005), Selective up-regulation of RB3/stathmin4 by ciliary neurotrophic factor following optic nerve axotomy, Brain Res, 1061(2):97-106.

Nickells (1996) "Retinal ganglion cell death in glaucoma: the how, the why, and the maybe," J. Glaucoma 5: 345-356.

Nickells et al. (1996) "Apoptosis of retinal ganglion cells in glaucoma: An update of the molecular pathways involved in cell death," Survey Ophthalmol. 43(Suppl.): S151-161.

O'Connell (2001) "Role of Fas-FasL in inflammatory diseases," Expert Rev Mol Med. Dec. 10, 2001: 1-18 (www.ermm.cbcu.cam.ac.uk/01003969h.htm.

Oka et al. (2005) "Involvement of Calpain in Retinal Degeneration Induced By N-Methyl-N-Nitrosourea in the Rats," Invest. Ophthalmol. Vis. Sci. 2005 46: E-Abstract 5255.

Okuda et al. (2000) "Intrathecal administration of neutralizing antibody against Fas ligand suppresses the progression of experimental autoimmune encephalomyelitis", Biochem. Biphys. Res. Commun. 275(1):164-8.

Ortiz et al. (1999) "The Fas ligand/Fas system in renal injury," Nephrol Dial Transplant 14: 1831-1834.

Osborne et al. (1999) "Neuroprotection in relation to retinal ischemia and relevance to glaucoma," Survey Opthalmol. 43(Suppl.): S102-128.

Pachydaki et al. (2006) "Effect of Systemic Administration of FK506 in a Rat Model of Retinal Detachment," Invest. Ophthalmol. Vis. Sci. 47: E-Abstract 1045.

Park et al. (2000) "A second calcineurin binding site on the NFAT regulatory domain," Proc Natl Acad Sci USA 97: 7130-7135.

Pease et al. (2000) "Obstructed axonal transport of BDNF and its receptor TrkB in experimental glaucoma," Invest. Ophthalmol. Vis. Sci. 41(3): 764-774.

Perche et al. (2005) Light-induced retinal apoptosis is caspase-dependent, Invest Ophthalmol Vis Sci. 46: E-Abstract 1666.

Poulaki (2001) "Fas/Fas ligand-associated apoptosis in experimental autoimmune uveoretinitis in rodents: role of proinflammatory corticotropin-releasing hormone," Exp Eye Res. 72(6):623-9.

Poulaki et al. (2005) "Anti-FasL Neutralizing Antibody Increases the Efficacy of PDT and Reduces the Apoptotic Damage in a Rat Laser Model," Invest Ophthalmol Vis Sci. 46: E-Abstract 185.

Quigley (1996) "Number of people with glaucoma worldwide," Br J Ophthalmol. 80: 389-393.

Quigley et al. (1995) "Retinal ganglion cell death in experimental glaucoma and after axotomy occurs by apoptosis," Invest. Ophthalmol. Visual Sci. 36(5): 774-786.

Raivich et al. (2003), Lymphocyte infiltration in the injured brain: role of proinflammatory cytokines, J Neurosci Res, 72:726-33.

Rao et al. (1997) "Transcription factors of the NFAT family," Ann Rev Immunol. 15: 707-47.

Rieux-Laucat et al. et al. (2003) "Cell-death signaling and human disease", Curr. Opin. Immunol. 15(3): 325-31.

Rosenstiel et al. (2003) "Differential effects of immunophilin-ligands (FK506 and V-10,367) on survival and regeneration of rat retinal ganglion cells in vitro and after optic nerve crush in vivo," J Neurotrauma 20(3):297-307.

Schulze-Osthoff et al. (1998) "Apoptosis signaling by death receptors," Eur J Biochem. 254(3):439-59.

Schwartz et al. (1996) "Potential treatment modalities for glaucomatous neuropathy: neuroprotection and neuroregeneration," J. Glaucoma 5: 427-432.

Seitz et al. (2002) "Localization and characterization of calcineurin in bovine eye," Invest. Ophthalmol. Visual Sci. 43: 15-21.

Shibasaki et al. (1996) Role of kinases and the phospahatease calcineurin inthe nuclear shuttling of transcription factor NF-AT4. Nature 382: 370-373.

Sobrin et al. (2004) "Pigment epithelial-derived factor (PEDF) inhibits apoptosis in a rat model of retinal detachment," the Aging Eye ARVO 2004 Annual Meeting, Program#/Poster#: 2064/B875.

Springer et al. (2000) "Calcineurin-mediated BAD dephosphorylation activates the caspase-3 apoptotic cascade in traumatic spinal cord injury," J. Neurosci. 20: 7246-7251.

Steiner et al. (1992) "High brain densities of the immunophilin FKBP colocalized with calcineurin," Nature 358: 584-587.

Stys et al. (2005), General mechanisms of axonal damage and its prevention, J Neurol Sci, 233:3-13.

Terada (2003) "Inhibition of excitatory neuronal cell death by cell-permeable calcineurin autoinhibitory peptide," J Neurochem. 87(5): 1145-51.

Tezel G, Yang X, Yang J, Wax MB. Role of tumor necrosis factor receptor-1 in the death of retinal ganglion cells following optic nerve crush injury in mice. Brain Res. Jan. 23, 2004;996(2):202-212.

Tompa et al. (2004) "On Sequential Determinants of Calpain Cleavage," J. Biol. Chem. 279(20): 20775-85.

Travis (1998) "Mechanisms of cell death in the inherited retinal degenerations," Am. J. Hum. Genet. 62(3): 503-508.

Tsujikawa et al. (1998) "Tacrolimus (FK506) attenuates leukocyte accumulation after transient retinal ischemia," Stroke 29(7): 1431-38.

Vorwerk et al. (1996) "Chronic low-dose glutamate is toxic to retinal ganglion cells. Toxicity blocked by memantine," Invest. Ophthalmol. Vis. Sci. 37: 1618-1624.

Vorwerk et al. (1999) "An experimental basis for implicating excitotoxicity in glaucomatous optic neuropathy," Survey Opthalmol. 43(Suppl.): S142-150.

Wang et al. (1989) "Characterization of the fragmented forms of calcineurin produced by calpain I," Biochem Cell Biol. 67(10): 703-11.

Wang et al. (1996) "An alpha-mercaptoacrylic acid derivative is a selective nonpeptide cell-permeable calpain inhibitor and is neuroprotective," PNAS 93: 6687-6692.

Wang et al. (1999) "Ca2+-induced apoptosis through calcineurin dephosphorylation of BAD," Science 284(5412): 339-43.

Wang et al. (2000) "Calpain and caspase: can you tell the difference?" TINS 23(1): 20-26.

Wax et al. (1998) "Clinical and ocular histopathological findings in a patient with normal-pressure glaucoma," Arch. Ophthalmol. 116: 993-1001.

Wen et al. (1995) "Injury-induced upregulation of bFGF and CNTF mRNAS in the rat retina," J. Neurosci. 15: 7377-7385.

Wen et al. (1996) "Alpha 2-adrenergic agonists induce basic fibroblast growth factor expression in photoreceptors in vivo and ameliorate light damage," J. Neurosci. 16: 5986-5992.

Wigginton et al. (2001) "IFN-gamma and Fas/FasL are required for the antitumor and antiangiogenic effects of IL-12/pulse IL-2 therapy," J. Clin. Invest. 108: 51-62.

Winter et al. (2000) "The immunophilin ligand FK506, but not GPI-1046, protects against neuronal death and inhibits c-Jun expression in the substantia nigra pars compacta following transection of the rat medial forebrain bundle," Neuroscience 95: 753-762.

Wu et al. (2004) "Critical role of calpain-mediated cleavage of calcineurin in excitotoxic neurodegeneration," J Biol Chem 279(6): 4929-40.

Young et al. (2004) "Modulation of Apoptosis Following Combination PEDF and Photodynamic Therapy for Choroidal Neovascularization in the Rat Model," Invest Opthalmol Vis Sci. 45: E-Abstract 2231.

Yuan et al. (2001) "Activated microglia in the human glaucomatous optic nerve head," J Neurosci Res 64: 523-32.

Zacks et al. (2004) "FAS-mediated apoptosis and its relation to intrinsic pathway activation in an experimental model of retinal detachment," Invest. Ophthalmol. Vis. Sci. 45(12): 4563-69.

Zacks et al. (2007) "Role of the FAS-signaling pathway in photoreceptor neuroprotection," Arch. Ophthalmol. 125(10): 1389-1395.

Zacks, et al. (2003) "Caspase Activation in an Experimental Model of Retinal Detachment Invest," Ophthalmol. Vis. Sci. 44: 1262-1267.

Zhang X, Chintala SK. Influence of interleukin-1 beta induction and mitogen-activated protein kinase phosphorylation on optic nerve ligation-induced matrix metalloproteinase-9 activation in the retina. Exp Eye Res. (2004) vol. 78(4):849-860.

Chen et al. (2002) "Photodynamic Therapy with Hypericin Induces Vascular Damage and Apoptosis in the RIF-1 mouse Tumor Model," Int. J. Cancer 98:284-90.

Chung et al. (2005) "Ankyrin Repeat and SOCS Box 3 (ASB3) Mediates Ubiquitination and Degradation of Tumor Necrosis Factor Receptor II," Molecular and Cellular Biology 25(11):4716-26.

Drolet et al. (2000) "Pharmacokinetics and Safety of an Anti-Vascular Endothelial Growth Factor Aptamer (NX1838) Following Injection into the Vitreous Humor of Rhesus Monkey," Pharm. Res. 17(12):1503-10.

Fuchs et al. (2005) "Retinal-cell-conditioned Medium Prevents TNF-alpha-induced Apoptosis of Purified Ganglion Cells," IOVS 46(8):2983-91.

Gu et al. (2005) "Endogenous TNF alpha Mediates Cell Survival and Chemotherapy Resistance by Activating the PI3K/Akt Pathway in Childhood Acute Lymphoblastic Leukemia," Blood 106(11):216B.

Healthcare Republic News, "Glaucoma Damage Reduced by Rheumatoid Arthritis Drugs," Dec. 8, 2006.

Horie et al. (1999) "Interferon-gamma Rescues TNF-alpha Induced Apoptosis Mediated by Up-regulation of TNFR2 on EoL-1 Cells," Experimental Hematology 27:512-9.

Mitsiades et al. (2001) "Matric Metalloproteinase-7-Meidated Cleavage of Fas Ligand Protects Tumor Cells from Chemotherapeutic Drug Toxicity," Cancer Res. 61:577-81.

Nakazawa et al. (2006), "Tumor Necrosis Factor-alpha Mediates Oligodendrocyte Death and Delayed Retinal Ganglion Cell Loss in a Mouse Model of Glaucoma," J. of Neuroscience 26(49):12633-41.

Saurenmann et al. (2006) "Tumour Necrosis Factor alpha Inhibitors in the Treatment of Childhood Uveitis," Rheumatology 45(8):982-9.

Tezel et al. (2000) "Increased Production of Tumor Necrosis Factor-alpha by Glial Cells Exposed to Simulated Ischemia or Elevated Hydrostatic Pressure Induces Apoptosis in Cocultured Retinal Ganglion Cells," J. of Neuroscience 20(23):8693-700.

Mitchell et al. (1996) Ophthalmology 103: 1661-1669.

Nakazawa et al. (2001) "Localization of calcineurin in the mature and developing retina," J Histochem Cytochem. 49(2): 187-195.

Shindo et al. (2003) "Intravitreal injection of tacrolimus (FK506) suppresses experimental uveitis without damaging the retina in rabbit," Invest Ophthalmol Vis Sci. 44: E-Abstract 4595.

Sommer et al. (1991) Arch. Ophthalmol. 109:, 1090-1095.

Ji et al. (2005) "Effects of elevated intraocular pressure on mouse retinal ganglion cells," Vision Res. 45:169-79.

Levkovitch-Verbin et al. (2006) "Minocyline Delays Death of Retinal Ganglion Cells in Experimental Glaucoma and After Optic Nerve Transection," Arch Ophthalmol. 124:520-26.

Aoudjit et al. (2001) Matrix attachment regulates Fas-induced apopotosis in endothelial cells: a role for c-flip and implications for anoikis J. Cell Biol. 152(3):633-43, abstract.

Eberl et al. (2000) "Endothelin receptor blockade potentiates FasL-induced apoptosis in colon carcinoma cells via the protein kinase C-pathway" J Cardiovasc Pharmacol. 36(5 Suppl 1):S354-6, abstract.

Eberl et al. (2000) "Endothelin receptor blockade potentiates FasL-induced apoptosis in rat colon carcinoma cells" Int. J. Cancer 86: 182-7, abstract.

Granville et al. (1999) "Bcl-2 overexpression blocks caspase activation and downstream apoptotic events instigated by photodynamic therapy" Br J Cancer 79(1): 95-100.

Han et al. (2004) "Effects of the combined use of benazepril and valsartan on apoptosis in the kidney of rats with adriamycin-induced nephritic glomerulosclerosis" Huazhong Univ. Sci. Technolog. Med. Sci. 24: 254-8, abstract.

Hasegawa et al. (2004) "Fas-disabling small exocyclic peptide mimetics limited aptopsis by an unexpected mechanism" Proc. Natl. Acad. Sci. U.S.A. 101(17):6599-604, abstract.

Ivanov et al. (1997) "Regulation of Fas-dependent activation-induced T cell apoptosis by cAMP signaling: a potential role for transcription factor NF-kappaB" Oncogene 14: 2455-64, abstract.

Le et al. (2002) "PAC1 and PACAP expression, signaling, and effect on the growth of HCT8, human colonic tumor cells" Regul Pept. 15;109(1-3):115-125, abstract.

Makrigiannakis et al. (2004) "Endometrial and placental CRH as regulators of human embryo implantation" J. Reprod. Immunol. 62:53-9, abstract.

Makrigiannakis et al. (2004) "Participation of maternal and fetal CRH in early phases of human implantation: the role of antalarmin" Current Drug Targets Immune Endoc. Matabol. Disord. 4(1):75-8, abstract.

Miller et al. (1999) "Photodynamic therapy with verteporfin for choroidal neovascularisation caused by age-related macular degeneration: Results of a single treatment in a phase 1 and 2 study" Arch. Ophthalmol. 117:1161-73.

Murohisa et al. (2002) "Involvement of platelet-activating factor in hepatic apoptosis and necrosis in chronic ethanol-fed rats given endotoxin" Liver 22:394-403, abstract.

Quirk et al. (2004) "Progesterone receptor and the cell cycle modulate apoptosis in granulosa cells" Endocrinology 145:5033-43, abstract.

Nyhus et al. (2001) "Direct in vivo transfection of antisense Fas-ligand reduces tumor growth and invasion" Gene Therapy 8, pp. 209-214.

Wortinger et al. (2003) "Fas ligand-induced murine pulmonary inflammation is reduced by a stale decoy receptor 3 analogue" Immunology 110(2):225-33.

Yu et al. (2001) "Pharmacokinetics and Pharmacodynamics of an Antisense Phosphorothioate Oligonucleotide Targeting Fas mRNA in Mice" J. of Pharmacology and Experimental Therapeutics, vol. 296, No. 2, pp. 388-395.

Zacks et al. (2002) "Verteporfin photodynamic therapy in the rat model of choroidal neovascularization: angiographic and histologic characterization" Invest Ophthalmol Vis Sci. 43(7):2383-2391.

Zou et al. (2007) "Lack of Fas antagonism by Met in human fatty liver disease" Nature, vol. 13, No. 9, 1078-1085.

Song et al. (2003) "RNA interference targeting Fas protects mice from fulminant hepatitis," Nature Medicine, 9, pp. 347-351 (Abstract).

Wang et al. (2003) "Fas siRNA reduces apoptotic cell death of allogenic-transplanted hepatocytes in mouse spleen," Transplant Proc. 35(4) pp. 1594-1595 (Abstract).

Yin (2000) "Signal transduction mediated by Bid, a pro-death Bcl-2 family proteins, connects the death receptor and mitochondria apoptosis pathways," Cell Research, 10, pp. 161-167.

Zhang et al. (2000) "Reduction of liver Fas expression by an antisense oligonucleotide protects mice from fulminant hepatitis," Nat Biotechnol. 18(8) pp. 862-867 (Abstract).

```
                        SEQUENCE LISTING

<160> NUMBER OF SEQ ID NOS: 6

<210> SEQ ID NO 1
<211> LENGTH: 19
<212> TYPE: PRT
<213> ORGANISM: Artificial Sequence
<220> FEATURE:
<223> OTHER INFORMATION: Caspase 1 inhibitor
<220> FEATURE:
<221> NAME/KEY: misc_feature
<222> LOCATION: (1)..(1)
<223> OTHER INFORMATION: X is Ac-Ala.
<220> FEATURE:
<221> NAME/KEY: misc_feature
<222> LOCATION: (19)..(19)
<223> OTHER INFORMATION: X is Asp-aldehyde.

<400> SEQUENCE: 1

Xaa Ala Val Ala Leu Leu Pro Ala Val Leu Leu Ala Leu Leu Pro Tyr
1               5                   10                  15

Val Ala Xaa

<210> SEQ ID NO 2
<211> LENGTH: 20
<212> TYPE: PRT
<213> ORGANISM: Artificial Sequence
<220> FEATURE:
<223> OTHER INFORMATION: Caspase 3 inhibitor
<220> FEATURE:
<221> NAME/KEY: misc_feature
<222> LOCATION: (1)..(1)
<223> OTHER INFORMATION: X is Ac-Ala.
<220> FEATURE:
<221> NAME/KEY: misc_feature
<222> LOCATION: (20)..(20)
<223> OTHER INFORMATION: X is Asp-aldehyde.

<400> SEQUENCE: 2

Xaa Ala Val Ala Leu Leu Pro Ala Val Leu Leu Ala Leu Leu Ala Pro
1               5                   10                  15

Asp Glu Val Xaa
            20

<210> SEQ ID NO 3
<211> LENGTH: 20
<212> TYPE: PRT
<213> ORGANISM: Artificial Sequence
<220> FEATURE:
<223> OTHER INFORMATION: Caspase 4 inhibitor
<220> FEATURE:
<221> NAME/KEY: misc_feature
<222> LOCATION: (1)..(1)
<223> OTHER INFORMATION: X is Ac-Ala.
<220> FEATURE:
<221> NAME/KEY: misc_feature
<222> LOCATION: (20)..(20)
<223> OTHER INFORMATION: X is Pro-aldehyde.

<400> SEQUENCE: 3

Xaa Ala Val Ala Leu Leu Pro Ala Val Leu Leu Ala Leu Leu Ala Pro
1               5                   10                  15
```

```
Leu Glu Ile Xaa
            20

<210> SEQ ID NO 4
<211> LENGTH: 20
<212> TYPE: PRT
<213> ORGANISM: Artificial Sequence
<220> FEATURE:
<223> OTHER INFORMATION: Caspase 6 inhibitor
<220> FEATURE:
<221> NAME/KEY: misc_feature
<222> LOCATION: (1)..(1)
<223> OTHER INFORMATION: X is Ac-Ala.
<220> FEATURE:
<221> NAME/KEY: misc_feature
<222> LOCATION: (20)..(20)
<223> OTHER INFORMATION: X is Asp-aldehyde.

<400> SEQUENCE: 4

Xaa Ala Val Ala Leu Leu Pro Ala Val Leu Leu Ala Leu Leu Ala Pro
1               5                  10                  15

Val Glu Ile Xaa
            20

<210> SEQ ID NO 5
<211> LENGTH: 20
<212> TYPE: PRT
<213> ORGANISM: Artificial Sequence
<220> FEATURE:
<223> OTHER INFORMATION: Caspase 8 inhibitor
<220> FEATURE:
<221> NAME/KEY: misc_feature
<222> LOCATION: (1)..(1)
<223> OTHER INFORMATION: X is AC-ALA
<220> FEATURE:
<221> NAME/KEY: misc_feature
<222> LOCATION: (20)..(20)
<223> OTHER INFORMATION: X is Asp-aldehyde.

<400> SEQUENCE: 5

Xaa Ala Val Ala Leu Leu Pro Ala Val Leu Leu Ala Leu Leu Ala Pro
1               5                  10                  15

Ile Glu Tyr Xaa
            20

<210> SEQ ID NO 6
<211> LENGTH: 20
<212> TYPE: PRT
<213> ORGANISM: Artificial Sequence
<220> FEATURE:
<223> OTHER INFORMATION: Caspase 9 inhibitor
<220> FEATURE:
<221> NAME/KEY: misc_feature
<222> LOCATION: (1)..(1)
<223> OTHER INFORMATION: X is Ac-Ala.
<220> FEATURE:
<221> NAME/KEY: misc_feature
<222> LOCATION: (20)..(20)
<223> OTHER INFORMATION: X is Asp-aldehyde.

<400> SEQUENCE: 6

Xaa Ala Val Ala Leu Leu Pro Ala Val Leu Leu Ala Leu Leu Ala Pro
1               5                  10                  15

Leu Glu His Xaa
            20
```

METHODS FOR PRESERVING THE VIABILITY OF PHOTORECEPTOR CELLS BY ANTI-FAS-LIGAND/ANTI-FAS-RECEPTOR ANTIBODIES

RELATED APPLICATIONS

This application is a continuation-in-part of International Application No. PCT/US03/01648, filed Jan. 17, 2003, which claims the benefit of U.S. Provisional Application No. 60/349,918, filed Jan. 18, 2002, the entire disclosures of which are incorporated by reference herein.

STATEMENT REGARDING FEDERALLY SPONSORED RESEARCH OR DEVELOPMENT

The U.S. Government may have certain rights in this invention as provided for by the terms of Grant No. K08 EY-14705, awarded by the National Eye Institute.

FIELD OF THE INVENTION

The invention relates generally to compositions and their use for preserving the viability of photoreceptor cells following retinal detachment, and more particularly the invention relates to compositions comprising an apoptosis inhibitor and their use in maintaining the viability of photoreceptor cells following retinal detachment.

BACKGROUND

The retina is a delicate neural tissue lining the back of the eye that converts light stimuli into electric signals for processing by the brain. Within the eye, the retina is disposed upon underlying retinal pigment epithelium and choroid, which provide the retina with a supply of blood and nutrients. A common and potentially blinding condition known as retinal detachment occurs when the retina becomes disassociated from its underlying retinal pigment epithelium and/or choroid with the accumulation of fluid in the intervening space. The loss of visual function appears to be more pronounced when the retinal detachments involve the central macula.

Unless treated, retinal detachments often result in irreversible visual dysfunction, which can range from partial to complete blindness. The visual dysfunction is believed to result from the death of photoreceptor cells, which can occur during the period when the retina is detached from its underlying blood and nutrient supply. Reattachment of the retina to the back surface of the eye typically is accomplished surgically, and despite the good anatomical results of these surgeries (i.e., reattachment of the retina) patients often are still left with permanent visual dysfunction.

There is still a need for new methods and compositions for maintaining the viability of photoreceptor cells following retinal detachment and for preserving vision when the retina ultimately becomes reattached.

SUMMARY

It is understood that photoreceptor cells in the retina may die via a variety of cell death pathways, for example, via apoptotic and necrotic cell death pathways. It has been found, however, that upon retinal detachment, the photoreceptor cells predominantly undergo apoptotic cell death in the detached portion of the retina. In addition, it has been found that, among other things, one or more caspases, for example, caspase 3, caspase 7, caspase 8, and caspase 9, participate in the cascade of events leading to apoptotic cell death.

In one aspect, the invention provides a method of preserving the viability of photoreceptor cells in a mammalian eye following retinal detachment. More particularly, the invention provides a method of preserving the viability of photoreceptor cells disposed within a region of a retina that has become detached from its underlying retinal pigment epithelium and/or choroid. The method comprises administering to a mammal in need of such treatment an amount of an apoptosis inhibitor sufficient to preserve the viability of photoreceptor cells, for example, rods and/or cones, disposed within the region of the detached retina. Administration of the apoptosis inhibitor minimizes the loss of visual function resulting from the retinal detachment. The apoptosis inhibitor reduces the number of photoreceptor cells in the region of the retina that, without treatment, would die following retinal detachment.

Useful apoptosis inhibitors include agents capable of modulating, for example, the receptor mediated pathway and/or the intrinsic pathway. Useful apoptosis inhibitors include agents capable of modulating the activity of a caspase selected from the group consisting of caspase 3, caspase 7, caspase 8, and caspase 9. Furthermore, it is contemplated that, under certain circumstances, it can be advantageous to administer along with the apoptosis inhibitor, another neuroprotective agent, for example, another apoptosis inhibitor or a neurotrophic factor.

In another aspect, the invention provides a method of preserving the viability of photoreceptor cells in a mammalian eye following retinal detachment. More particularly, the invention provides a method of preserving the viability of photoreceptor cells disposed within a region of a retina that has become detached from its underlying retinal pigment epithelium and/or choroid. The method comprises administering to a mammal in need of such treatment an amount of a caspase inhibitor, for example, a caspase 3 inhibitor, a caspase 7 inhibitor, a caspase 8 inhibitor or a caspase 9 inhibitor, or a combination of two or more of such caspase inhibitors, sufficient to preserve the viability of photoreceptor cells disposed within the region of the detached retina.

Because photoreceptors die as a result of retinal detachment, administration of the apoptosis inhibitor minimizes or reduces the loss of photoreceptor cell viability until such time the retina becomes reattached to the choroid and an adequate blood and nutrient supply is once again restored. The apoptosis inhibitor minimizes the level of photoreceptor cell death, and maintains photoreceptor cell viability prior to reattachment of the detached region of the retina. Under certain circumstances, however, it may be beneficial to administer the apoptosis inhibitor for a period of time after a retinal detachment has been detected and/or the retina surgically reattached. This period of time may vary depending on the circumstances and can include, for example, a period of a week, two weeks, three weeks, a month, three months, six months, nine months, a year, and two years, after surgical reattachment.

The apoptosis inhibitor, for example, a caspase inhibitor, can be administered, either alone or in combination with a pharmaceutically acceptable carrier or excipient, by one or more routes. For example, the apoptosis inhibitor may be administered systemically, for example, via oral or parenteral routes, for example, via intravascular, intramuscular or subcutaneous routes. Alternatively, the apoptosis inhibitor may be administered locally, for example, via intraocular, intravitreal, intraorbital, subretinal, or transcleral routes. Furthermore, it is contemplated that the apoptosis inhibitor, for example, a caspase inhibitor, may be administered with another type of neuroprotective agent, for example, a neurotrophic factor, to maintain viability of the photoreceptor cells disposed within the detached portion of the retina. The apoptosis inhibitor and the neuroprotective agent may be co-administered either simultaneously or one after the other, for example, the apoptosis inhibitor is administered after the neuroprotective agent or the neuroprotective agent is administered after the apoptosis inhibitor.

It is contemplated that the practice of the invention will be helpful in maintaining the viability of photoreceptor cells in retinal detachments irrespective of how the retinal detachments were caused. For example, it is contemplated that the practice of the method of the invention will be helpful in minimizing visual dysfunction resulting from retinal detachments caused by one or more of the following: a retinal tear, retinoblastoma, melanoma, diabetic retinopathy, uveitis, choroidal neovascularization, retinal ischemia, pathologic myopia, and trauma.

In another aspect, the invention provides an improved method of reattaching a detached retina in a mammal, for example, a human. The improvement comprises administering, either locally to the eye or systemically, an apoptosis inhibitor in an amount sufficient to preserve the viability of photoreceptor cells in the eye. The apoptosis inhibitor can be a caspase inhibitor, for example, a caspase 3 inhibitor, a caspase 7 inhibitor, a caspase 8 inhibitor, or a caspase 9 inhibitor. The method may also comprise co-administering the apoptosis inhibitor with a neuroprotective agent, for example, a neurotrophic factor.

The foregoing aspects and embodiments of the invention may be more fully understood by reference to the following figures, detailed description and claims.

BRIEF DESCRIPTION OF THE DRAWINGS

The objects and features of the invention may be more fully understood by reference to the drawings described below in which.

DETAILED DESCRIPTION

Figure 1:
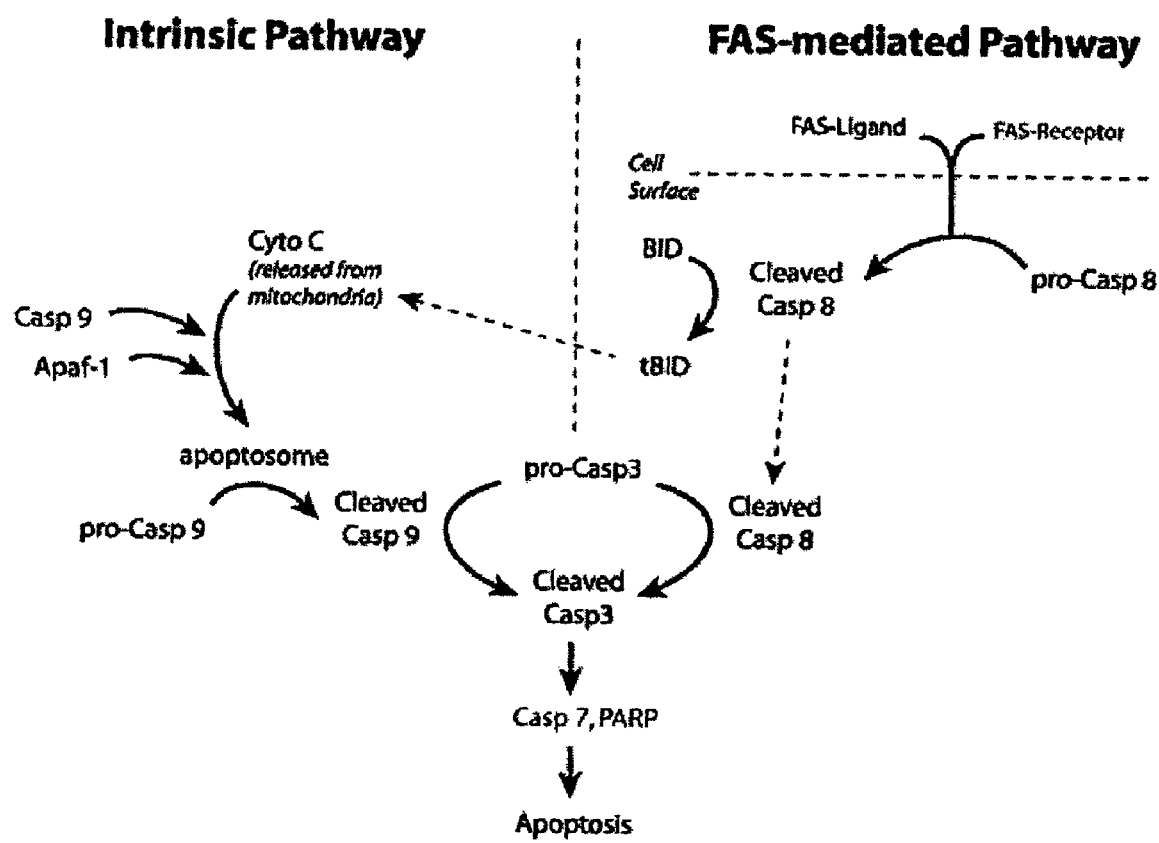
FIG. 1 is a schematic representation of the intrinsic and the FAS-mediated apoptosis pathways, however, for clarity some of the intermediates in each pathway are not shown and the abbreviations include Cyto C-cytochrome C, Apaf-1—apoptosis activating factor 1, Casp 3—caspase 3, Casp 7—caspase 7, Casp 8—caspase 8, Casp9—caspase 9, tBID—truncated BID, and PARP—poly-ADP ribose-polymerase.

During retinal detachment, the entire retina or a portion of the retina becomes dissociated from the underlying retinal pigment epithelium and choroid. As a result, the sensitive photoreceptor cells disposed in the detached portion of the retina become deprived of their normal supply of blood and nutrients. If untreated, the retina or more particularly the sensitive photoreceptor cells disposed within the retina die causing partial or even complete blindness. Accordingly, there is an ongoing need for methods and compositions that preserve the viability of photoreceptor cells following retinal detachment. If photoreceptor cell death can be minimized during retinal detachment, the affected photoreceptors likely will survive once the retina is reattached to the underlying retinal pigment epithelium and choroid, and the photoreceptors regain their normal blood and nutrient supply.

Retinal detachment can occur for a variety of reasons. The most common reason for retinal detachment involves retinal tears. Retinal detachments, however, can also occur because of, for example, retinoblastomas and other ocular tumors (for example, angiomas, melanomas, and lymphomas), diabetic retinopathy, retinal vascular diseases, uveitis, retinal ischemia and trauma. Furthermore, retinal detachments can occur as a result of formation of choroidal neovascularizations secondary to, for example, the neovascular form of age-related macular degeneration, pathologic myopia, and ocular histoplasmosis syndrome. It is understood that the clinical pathologies of retinal detachments are different from those of degenerative retinal disorders, for example, retinitis pigmentosa and age-related macular degeneration. However, the apoptosis inhibitors discussed herein may be useful in treating retinal detachments that occur secondary to an underlying degenerative retinal disorder. Accordingly, it is contemplated that the methods and compositions of the invention may be useful in minimizing or otherwise reducing photoreceptor cell death following retinal detachment, irrespective of the cause of the detachment.

It is understood that photoreceptor cell death during retinal detachments may occur as a result of either necrotic or apoptotic (also known as programmed cell death) pathways. Both of these pathways are discussed in detail in, for example, Kerr et al. (1972) BR. J. CANCER 26: 239-257, Wyllie et al. (1980) INT. REV. CYTOLOGY 68: 251-306; Walker et al. (1988) METH. ACHIE. EXP. PATHOL. 13: 18-54 and Oppenheim (1991) ANN. REV. NEUROSCI. 14: 453-501. Apoptosis involves the orderly breakdown and packaging of cellular components and their subsequent removal by surrounding structures (Afford &

Randhawa (2000) J. CLIN. PATHOL. 53:55-63). In general, apoptosis, also referred to as an apoptotic pathway, does not result in the activation of an inflammatory response. This is in contrast to necrotic cell death, which is characterized by the random breakdown of cells in the setting of an inflammatory response. Typically, during necrosis, also known as a necrotic pathway, a catastrophic event, for example, trauma, inflammation, ischemia or infection, typically causes uncontrolled death of a large group of cells. There are a variety of assays available for determining whether cell death is occurring via a necrotic pathway or an apoptotic pathway (see, for example, Cook et al. (1995) INVEST. OPHTHALMOL. VIS. SCI. 36:990-996).

Apoptosis involves the activation of a genetically determined cell suicide program that results in a morphologically distinct form of cell death characterized by cell shrinkage, nuclear condensation, DNA fragmentation, membrane reorganization and blebbing (Kerr et al. (1972) BR. J. CANCER 26: 239-257). Assays for detecting the presence of apoptotic pathways include measuring morphologic and biochemical stigmata associated with cellular breakdown and packaging, such as pyknotic nuclei, apoptotic bodies (vesicles containing degraded cell components) and internucleosomally cleaved DNA. This last feature is specifically detected by binding and labeling the exposed 3'-OH groups of the cleaved DNA with the enzyme terminal deoxynucleotidyl transferase in the staining procedure often referred to as the TdT-dUTP Terminal Nick End-Labeling (TUNEL) staining procedure. It is believed that, at the core of this process lies a conserved set of serine proteases, called caspases, which are activated specifically in apoptotic cells.

In general, during retinal detachment as shown in FIG. 1, apoptosis is activated by one of two main pathways, the receptor-mediated pathway (Walczak & Krammer (2000) EXP. CELL RES. 256: 58-66) and the intrinsic (mitochondrial) pathway (Loeffler & Kroemer (2000) EXP. CELL RES. 256: 19-26). The receptor mediated pathway is understood to involve the components of the FAS/FAS-ligand system; the prototypical receptor-mediated apoptosis pathway. Both FAS and FAS-ligand are surface membrane proteins that belong to the tumor necrosis factor-α superfamily of proteins (Love (2003) PROG. NEURO. BIOL. PSYCH. 27: 267-82). As shown in FIG. 1, cleaved caspase 8 can either directly activate caspase 3 or directly activate BID, a member of the Bcl-2 family of proteins, which in turn then feeds into the intrinsic pathway by stimulating the release of mitochondrial cytochrome C.

In addition to the receptor-mediated pathway, apoptosis can also become activated via an intrinsic pathway. It is understood that the intrinsic pathway does not involve a surface receptor, but rather results from the modification of intracellular pools of proteins. Such modulators include BID (activated by the FAS-mediated pathway) as well as other members of the Bcl-2 family. Environmental or intracellular stressors result in post-translation modification of these proteins, which then exert their effect on the mitochondria to release cytochrome C. It is understood that the released cytochrome C then binds with apoptosis activating factor-1 and caspase 9 to form a complex known as the apoptosome, which in turn activates more downstream apoptosis reactions. In particular, the apoptosome, can induce the conversion of pro-caspase 9 into active cleaved caspase 9, which itself then induces the conversion of pro-caspase 3 into active cleaved caspase 3. Activated caspase 3 (either activated by the FAS-mediated pathway or the intrinsic pathway) then initiates apoptosis optionally via intermediates caspase 7 and PARP.

The invention provides a method of preserving the viability of photoreceptor cells in a mammalian, for example, a primate, for example, a human, eye following retinal detachment. More particularly, the invention provides a method of preserving the viability of photoreceptor cells disposed within a region of a retina, which has become detached from its underlying retinal pigment epithelium and/or choroid. The method may be particularly helpful in preventing vision loss when the region of detachment includes at least a portion of the macula. The method comprises administering to a mammal in need of such treatment an amount of an apoptosis inhibitor sufficient to preserve the viability of photoreceptor cells disposed within the region of the detached retina. The apoptosis inhibitor is capable of modulating, for example, decreasing, the activity of one or more of caspase 3, caspase 7, caspase 8 and caspase 9, and/or preventing or reducing the activation of one or more of caspase 3, caspase 7, caspase 8, and caspase 9.

As used herein, the term "apoptosis inhibitor" is understood to mean any agent other than a naturally occurring neurotrophic factor that, when administered to a mammal, reduces apoptotic cell death in photoreceptor cells. It is understood that the apoptosis inhibitor excludes certain naturally occurring neurotrophic factors, including brain-derived neurotrophic factor, glial cell line-derived neurotrophic factor, neurotrophin, insulin-like growth factor, ciliary neurotrophic factor, fibroblast growth factor (acidic and basic), transforming growth factor α, and transforming growth factor β. It is understood that certain useful apoptosis inhibitors act by reducing or eliminating the activity of one or more members of the intrinsic apoptotic pathway and/or the FAS-mediated apoptotic pathway. For example, it is understood that an agent that inactivates or reduces the activity of the FAS-ligand and/or the FAS-receptor is considered to be an apoptosis inhibitor. Furthermore, it is understood that an agent that either directly or indirectly affects the activity of a particular caspase, for example, caspase 3, caspase 7, caspase 8, and caspase 9, is considered to be an apoptosis inhibitor.

There are approximately fourteen known caspases, and the activation of these proteins results in the proteolytic digestion of the cell and its contents. Each of the members of the caspase family possess an active-site cysteine and cleave substrates at Asp-Xxx bonds (i.e., after the aspartic acid residue). In general, a caspase's substrate specificity typically is determined by the four residues amino-terminal to the cleavage site. Caspases have been subdivided into subfamilies based on their substrate specificity, extent of sequence identity and structural similarities, and include, for example, caspase 1, caspase 2, caspase 3, caspase 4, caspase 5, caspase 6, caspase 7, caspase 8, caspase 9, caspase 10, caspase 11, caspase 12, caspase 13 and caspase 14. Monitoring their activity can be used to assess the level of on-going apoptosis.

Furthermore, it has been suggested that apoptosis is associated with the generation of reactive oxygen species, and that the product of the $Bcl_2$ gene protects cells against apoptosis by inhibiting the generation or the action of the reactive oxygen species (Hockenbery et al. (1993) CELL 75: 241-251, Kane et al. (1993) SCIENCE 262: 1274-1277, Veis et al. (1993) CELL 75: 229-240, Virgili et al. (1998) FREE RADICALS BIOL. MED. 24: 93-101). $Bcl_2$ belongs to a growing family of apoptosis regulatory gene products, which may either be death antagonists ($Bcl_2$, $Bcl-x_L$) or death agonists (Bax, Bak) (Kroemer et al. (1997) NAT. MED. 3: 614-620). Control of cell death appears to be regulated by these interactions and by constitutive activities of the various family members (Hockenbery et al. (1993) CELL 75: 241-251). Several apoptotic pathways may coexist in mammalian cells that are preferentially activated in a stimulus-, stage-, context-specific and cell-type manner (Hakem et al. (1998) CELL 94: 339-352). However, it is contemplated that agents that upregulate the level of the Bcl-2 gene expression or slow down the rate of breakdown of the Bcl-2 gene product may be useful in the practice of the invention.

Although photoreceptors may undergo either apoptotic cell death or necrotic cell death following retinal detachment it is believed that the primary mechanism of cell death is via apoptosis. Accordingly, apoptosis inhibitors preferably are used in the practice of the invention.

Useful apoptosis inhibitors include, for example, proteins, for example, cytokines, antibodies and antigen binding fragments thereof (for example, Fab, Fab', and Fv fragments), genetically engineered biosynthetic antibody binding sites, also known in the art as BABS or sFv's. Other useful apoptosis inhibitors include, for example, peptides, for example, an amino acid sequence less than about 25 amino acids in length, and optionally an amino acid sequence less than 15 amino acids in length. Peptides useful in the invention comprise, for example, synthetic peptides and derivatives thereof. Other useful apoptosis inhibitors include, for example, deoxyribose nucleic acids (for example, antisense oligonucleotides and aptamers), ribose nucleic acids (for example, antisense oligonucleotides and aptamers) and peptidyl nucleic acids, which once administered reduce or eliminate expression of certain genes, for example, caspase genes as in the case of anti-sense molecules, or can bind to and reduce or eliminate the activity of a target protein or receptor as in the case of aptamers. Other useful apoptosis inhibitors include small organic or inorganic molecules that reduce or eliminate apoptotic activity when administered to the mammal.

One set of apoptosis inhibitors useful in the practice of the invention include caspase inhibitors. Caspase inhibitors include molecules that inhibit or otherwise reduce the catalytic activity of a target caspase molecule (for example, a classical competitive or non-competitive inhibitor of catalytic activity) as well as molecules that prevent the onset or initiation of a caspase mediated apoptotic pathway.

With regard to the inhibitors of catalytic function, it is contemplated that useful caspase inhibitors include, on the one hand, broad spectrum inhibitors that reduce or eliminate the activity of a plurality of caspases or, on the other hand, specific caspase inhibitors that reduce or eliminate the activity of a single caspase. In general, caspase inhibitors act by binding the active site of a particular caspase enzyme and forming either a reversible or an irreversible linkage to target caspase molecule. Caspase inhibitors may include inhibitors of one or more of caspase 1, caspase 2, caspase 3, caspase 4, caspase 6, caspase 7, caspase 8, caspase 9, caspase 10, caspase 11, caspase 12, caspase 13, and caspase 14.

Useful caspase inhibitors include commercially available synthetic (i.e., non naturally occurring) caspase inhibitors. The synthetic caspase inhibitors may comprise less that 25, optionally less than 15, and optionally less than 10 amino acids or amino acid derivatives. Synthetic caspase inhibitors typically include a peptide recognition sequence attached to a functional group such as an aldehyde, chloromethylketone, fluoromethylketone, or fluoroacyloxymethylketone. Typically, synthetic caspase inhibitors with an aldehyde functional group reversibly bind to their target caspases, whereas the caspase inhibitors with the other functional groups tend to bind irreversibly to their targets. Useful caspase inhibitors, when modeled with Michaelis-Menten kinetics, preferably have a dissociation constant of the enzyme-inhibitor complex ($K_i$) lower than 100 µM, preferably lower than 50 µM, more preferably lower than 1 µM. The peptide recognition sequence corresponding to that found in endogenous substrates determines the specificity of a particular caspase. For example, peptides with the Ac-Tyr-Val-Ala-Asp-aldehyde sequence are potent inhibitors of caspases 1 and 4 ($K_i$=10 nM), and are weak inhibitors of caspases 3 and 7 ($K_i \geq 50$ µM). Removal of the tyrosine residue, however, results in a potent but less specific inhibitor. For example, 2-Val-Ala-Asp-fluoromethylketone inhibits caspases 1 and 4 as well as caspases 3 and 7.

Exemplary synthetic caspase 1 inhibitors, include, for example, Ac—N-Me-Tyr-Val-Ala-Asp-aldehyde, Ac-Trp-Glu-His-Asp-aldehyde, Ac-Tyr-N-Me-Val-Ala-N-Me-Asp-aldehyde, Ac-Tyr-Val-Ala-Asp-Aldehyde, Ac-Tyr-Val-Ala-Asp-chloromethylketone, Ac-Tyr-Val-Ala-Asp-2,6-dimethylbenzoyloxymethylketone, Ac-Tyr-Val-Ala-Asp (OtBu)-aldehyde-dimethyl acetol, Ac-Tyr-Val-Lys-Asp-aldehyde, Ac-Tyr-Val-Lys(biotinyl)-Asp-2,6-dimethylbenzoyloxymethylketone, biotinyl-Tyr-Val-Ala-Asp-chloromethylketone, Boc-Asp(OBzl)-chloromethylketone, ethoxycarbonyl-Ala-Tyr-Val-Ala-Asp-aldehyde (pseudo acid), Z-Asp-2,6-dichlorobenzoyloxymethylketone, Z-Asp(OlBu)-bromomethylketone, Z-Tyr-Val-Ala-Asp-chloromethylketone, Z-Tyr-Val-Ala-DL-Asp-fluoromethlyketone, Z-Val-Ala-DL-Asp-fluoromethylketone, and Z-Val-Ala-DL-Asp(OMe)-fluoromethylketone, all of which can be obtained from Bachem Bioscience Inc., PA. Other exemplary caspase 1 inhibitors include, for example, Z-Val-Ala-Asp-fluoromethylketone, biotin-X-Val-Ala-Asp-fluoromethylketone, Ac—Val-Ala-Asp-aldehyde, Boc-Asp-fluoromethylketone, Ac-Ala-Ala-Val-Ala-Leu-Leu-Pro-Ala-Val-Leu-Leu-Ala-Leu-Leu-Pro-Tyr-Val-Ala-Asp-aldehyde (SEQ ID NO: 1), biotin-Tyr-Val-Ala-Asp-fluoroacyloxymethylketone, Ac-Tyr-Val-Ala-Asp-acyloxymethylketone, Z-Asp-CH2-DCB, Z-Tyr-Val-Ala-Asp-fluoromethylketone, all of which can be obtained from Calbiochem, Calif.

Exemplary synthetic caspase 2 inhibitors, include, for example, Ac—Val-Asp-Val-Ala-Asp-aldehyde, which can be obtained from Bachem Bioscience Inc., PA, and Z-Val-Asp-Val-Ala-Asp-fluoromethylketone, which can be obtained from Calbiochem, Calif.

Exemplary synthetic caspase 3 precursor protease inhibitors include, for example, Ac-Glu-Ser-Met-Asp-aldehyde (pseudo acid) and Ac—Ile-Glu-Thr-Asp-aldehyde (pseudo acid) which can be obtained from Bachem Bioscience Inc., PA. Exemplary synthetic caspase 3 inhibitors include, for example, Ac-Asp-Glu-Val-Asp-aldehyde, Ac-Asp-Met-Gin-Asp-aldehyde, biotinyl-Asp-Glu-Val-Asp-aldehyde, Z-Asp-Glu-Val-Asp-chloromethylketone, Z-Asp(OMe)-Glu(OMe)-Val-DL-Asp(OMe)-fluoromethylketone, and Z-Val-Ala-DL-Asp(OMe)-fluoromethylketone which can be obtained from Bachem Bioscience Inc., PA. Other exemplary caspase 3 inhibitors include, for example, Ac-Ala-Ala-Val-Ala-Leu-Leu-Pro-Ala-Val-Leu-Leu-Ala-Leu-Leu-Ala-Pro-Asp-Glu-Val-Asp-aldehyde (SEQ ID NO: 2), biotin-X-Asp-Glu-Val-Asp-fluoromethylketone, Ac-Asp-Glu-Val-Asp-chloromethylketone, which can be obtained from Calbiochem, Calif. Another exemplary caspase 3 inhibitor includes, the caspase 3 inhibitor N-benzyloxycarbonal-Asp (OMe)-Glu(OMe)-Val-Asp(Ome)-fluoromethyketone (z-Asp-Glu-Val-Asp-fmk), which can be obtained from Enzyme Systems Products, CA.

Exemplary synthetic caspase 4 inhibitors include, for example, Ac-Leu-Glu-Val-Asp-aldehyde and Z-Tyr-Val-Ala-DL-Asp-fluoromethylketone, which can be obtained from Bachem Bioscience Inc., PA, and Ac-Ala-Ala-Val-Ala-Leu-Leu-Pro-Ala-Val-Leu-Leu-Ala-Leu-Leu-Ala-Pro-Leu-Glu-Val-Pro-aldehyde (SEQ ID NO: 3), which can be obtained from Calbiochem, Calif.

Exemplary synthetic caspase 5 inhibitors include, for example, Z-Trp-His-Glu-Asp-fluoromethylketone, which can be obtained from Calbiochem, Calif., and Ac-Trp-Glu-His-Asp-aldehyde and Z-Trp-Glu(O-Me)-His-Asp(O-Me) fluoromethylketone, which can be obtained from Sigma Aldrich, Germany.

Exemplary synthetic caspase 6 inhibitors include, for example, Ac-Val-Glu-Ile-Asp-aldehyde, Z-Val-Glu-Ile-Asp-fluoromethylketone, and Ac-Ala-Ala-Val-Ala-Leu-Leu-Pro-Ala-Val-Leu-Leu-Ala-Leu-Leu-Ala-Pro-Val-Glu-Ile-Asp-aldehyde (SEQ ID NO: 4), which can be obtained from Calbiochem, Calif.

Exemplary synthetic caspase 7 inhibitors include, for example, Z-Asp(OMe)-Gln-Met-Asp(OMe) fluoromethylketone, Ac-Asp-Glu-Val-Asp-aldehyde, Biotin-Asp-Glu-Val-Asp-fluoromethylketone, Z-Asp-Glu-Val-Asp-fluoromethylketone, Ac-Ala-Ala-Val-Ala-Leu-Leu-Pro-Ala-Val-Leu-Leu-Ala-Leu-Leu-Ala-Pro-Asp-Glu-Val-Asp-aldehyde (SEQ ID NO: 2), which can be obtained from Sigma Aldrich, Germany.

Exemplary synthetic caspase 8 inhibitors include, for example, Ac-Asp-Glu-Val-Asp-aldehyde, Ac—Ile-Glu-Pro-Asp-aldehyde, Ac—Ile-Glu-Thr-Asp-aldehyde, Ac-Trp-Glu-His-Asp-aldehyde and Boc-Ala-Glu-Va-Asp-aldehyde which can be obtained from Bachem Bioscience Inc., PA. Other exemplary caspase 8 inhibitors include, for example, Ac-Ala-Ala-Val-Ala-Leu-Leu-Pro-Ala-Val-Leu-Leu-Ala-Leu-Leu-Ala-Pro-Ile-Glu-Thr-Asp-aldehyde (SEQ ID NO: 5) and Z-Ile-Glu-Thr-Asp-fluoromethylketone, which can be obtained from Calbiochem, Calif.

Exemplary synthetic caspase 9 inhibitors, include, for example, Ac-Asp-Glu-Val-Asp-aldehyde, Ac-Leu-Glu-His-Asp-aldehyde, and Ac-Leu-Glu-His-Asp-chloromethylketone which can be obtained from Bachem Bioscience Inc., PA. Other exemplary caspase 9 inhibitors include, for example, Z-Leu-Glu-His-Asp-fluoromethylketone and Ac-Ala-Ala-Val-Ala-Leu-Leu-Pro-Ala-Val-Leu-Leu-Ala-Leu-Leu-Ala-Pro-Leu-Glu-His-Asp-aldehyde (SEQ ID NO:6), which can be obtained from Calbiochem, Calif.

Furthermore, it is contemplated that caspase specific antibodies (for example, monoclonal or polyclonal antibodies, or antigen binding fragments thereof), for example, an antibody that specifically binds to and reduces the activity of, or inactivates a particular caspase may be useful in the practice of the invention. For example, an anti-caspase 3 antibody, an anti-caspase 7 antibody, an anti-caspase 8 antibody, or an anti-caspase 9 antibody may be useful in the practice of the invention. Additionally, it is contemplated that an anti-caspase aptamer that specifically binds and reduces the activity of, or inactivates a particular caspase, for example, an anti-caspase 3 aptamer, an anti-caspase 7 aptamer, an anti-caspase 8 aptamer, or an anti-caspase 9 aptamer may be useful in the practice of the invention.

Alternatively, certain endogenous caspase inhibitors other than naturally occurring neurotrophic factors can be used to reduce, or inhibit caspase activity. For example, one useful class of endogenous caspase inhibitor includes proteins known as inhibitors of apoptosis proteins (IAPs) (Deveraux et al. (1998) EMBO J. 17(8): 2215-2223) including bioactive fragments and analogs thereof. One exemplary IAP includes X-linked inhibitor of apoptosis protein (XIAP), which has been shown to be a direct and selective inhibitor of caspase-3, caspase-7 and caspase-9. Another exemplary IAP includes survivin (see, U.S. Pat. No. 6,245,523; Papapetropoulos et al. (2000) J. BIOL. CHEM. 275: 9102-9105), including bioactive fragments and analogs thereof. Survivin has been reported to inhibit caspase-3 and caspase-7 activity.

Furthermore, by way of example, cAMP elevating agents may also serve as effective apoptosis inhibitors. Exemplary cAMP elevating agents include, for example, 8-(4-chlorophenylthio)-adenosine-3':5'-cyclic-monophosphate (CPT-cAMP) (Koike (1992) PROG. NEURO-PSYCHOPHARMACOL. BIOL. PSYCHIAT. 16: 95-106), forskolin, isobutyl methylxanthine, cholera toxin (Martin et al. (1992) J. NEUROBIOL. 23:1205-1220), and 8-bromo-cAMP, $N^6$, $O^{2'}$-dibutyryl-cAMP and $N^6,O^{2'}$dioctanoyl-cAMP (Rydel and Greene (1988) PROC. NAT. ACAD. SCI. USA 85: 1257-1261).

Furthermore, other exemplary apoptosis inhibitors can include, for example, glutamate inhibitors, for example, NMDA receptor inhibitors (Bamford et al. (2000) EXP. CELL RES. 256: 1-11) such as eliprodil (Kapin et al. (1999) INVEST. OPHTHALMOL. VIS. SCI 40,1177-82) and MK-801 (Solberg et al. INVEST. OPHTHALMOL. VIS. SCI (1997) 38,1380-1389) and n-acetylated-α-linked-acidic dipeptidase inhibitors, such as, 2-(phosphonomethyl) pentanedioic acid (2-PMPA) (Harada et al. NEUR. LETT. (2000) 292,134-36); steroids, for example, hydrocortisone and dexamethasone (see, U.S. Pat. No. 5,840,719; Wenzel et al. (2001) INVEST. OPHTHALMOL. VIS. SCI. 42: 1653-9); nitric oxide synthase inhibitors (Donovan et al. (2001) J. BIOL. CHEM. 276: 23000-8); serine protease inhibitors, for example, 3,4-dichloroisocoumarin and N-tosyl-lysine chloromethyl ketone (see, U.S. Pat. No. 6,180,402); cysteine protease inhibitors, for example, N-ethylmaleimide and iodoacetamide; and anti-sense nucleic acid or peptidyl nucleic acid sequences that lower of prevent the expression of one or more of the death agonists, for example, the products of the Bax, and Bak genes.

In addition, or in the alternative, it may be useful to inhibit expression or activity of members of the caspase cascade that are upstream or downstream of caspase 3, caspase 7 and caspase 9. For example, it may be useful to inhibit PARP, which is a component of the apoptosis cascade downstream of caspase 7. An exemplary PARP inhibitor includes 3-aminobenzamide (Weise et al. (2001) CELL DEATH DIFFER. 8:801-807). Other examples include inhibitors of the expression or activity of Apoptosis Activating Factor-1 (Apaf-1) and/or cytochrome C. Apaf-1 and cytochrome C bind the activated form of caspase 9 to produce the apoptosome complex, which is known to propagate the apoptosis cascade. Thus, any protein (for example, antibody), nucleic acid (for example, aptamer), peptidyl nucleic acid (for example, antisense molecule) or other molecule that inhibits or interferes with the binding of caspase 9 to Apaf-1/cytochrome C can serve to inhibit apoptosis.

It is contemplated that the foregoing and other apoptosis inhibitors now known or hereafter discovered may be assayed for efficacy in minimizing photoreceptor cell death following retinal detachment using a variety of model systems. Basic techniques for inducing retinal detachment in various animal models are known in the art (see, for example, Anderson et al. (1983) INVEST. OPHTHALMOL. VIS. SCI. 24: 906-926; Cook et al. (1995) INVEST. OPHTHALMOL. VIS. SCI. 36: 990-996; Marc et al. (1998) OPHTHALMOL. VIS. SCI. 39: 1694-1702; Mervin et al. (1999) AM. J. OPHTHALMOL. 128: 155-164; Lewis et al. (1999) AM. J. OPHTHALMOL. 128: 165-172). Once a suitable animal model has been created (see, Example 1 below) an established or putative apoptosis inhibitor can be administered to an eye at different dosages. The ability of the apoptosis inhibitor and dosage required to maintain cell viability may be assayed by one or more of (i) tissue histology, (ii) TUNEL staining, which quantifies the number of TUNEL positive cells per section, (iii) electron microscopy, (iv) immunoelectron microscopy to detect the level of, for example, apoptosis inducing factor (AIF) in the samples, and (v) immunochemical analyses, for example, via Western blotting, to detect the level of certain caspases in a sample.

The TUNEL technique is particularly useful in observing the level of apoptosis in photoreceptor cells. By observing the number of TUNEL positive cells in a sample, it is possible to determine whether a particular apoptosis inhibitor is effective at minimizing or reducing the level of apoptosis, or eliminating apoptosis in a sample. For example, the potency of the apoptosis inhibitor will have an inverse relationship to the number of TUNEL positive cells per sample. By comparing the efficacy of a variety of potential apoptosis inhibitors using these methods, it is possible to identify apoptosis inhibitors most useful in the practice of the invention.

In addition, the apoptosis inhibitor may be co-administered with a neuroprotective agent. As used herein, the term "neuroprotective agent" means any agent that, when administered to a mammal, either alone or in combination with other agents, minimizes or eliminates photoreceptor cell death in a region of the retina that has become detached from the underlying retinal pigment epithelium and/or choroid. It is contemplated that useful neuroprotective agents include, for example, apoptosis inhibitors, for example, caspase inhibitors, and certain neurotrophic factors that prevent the onset or progression of apoptosis. More specifically, useful neuroprotective agents may include, for example, a protein (for example a growth factor, antibody or an antigen binding fragment thereof), a peptide (for example, an amino acid sequence less than about 25 amino acids in length, and optionally an amino acid sequence less that about 15 amino acids in length), a nucleic acid (for example, a deoxyribose nucleic acid, ribose nucleic acid, an antisense oligonucleotide, or an aptamer), a peptidyl nucleic acid (for example, an antisense peptidyl nucleic acid), an organic molecule or an inorganic molecule, which upon administration minimizes photoreceptor cell death following retinal detachment.

It is contemplated that useful neuroprotective agents may include one or more neurotrophic factors. Exemplary neurotrophic factors include, for example, Brain Derived Growth Factor (Caffe et al. (2001) INVEST OPHTHALMOL. VIS. SCI. 42: 275-82) including bioactive fragments and analogs thereof; Fibroblast Growth Factor (Bryckaert et al. (1999) ONCOGENE 18: 7584-7593) including bioactive fragments and analogs thereof; Ciliary Neurotrophic Factor including bioactive fragments and analogs thereof; and Insulin-like Growth Factors, for example, IGF-1 and IGF-II (Rukenstein et al. (1991) J. NEUROSCI. 11:2552-2563) including bioactive fragments and analogs thereof; and cytokine-associated neurotrophic factors.

Bioactive fragments refer to portions of an intact template protein that have at least 30%, more preferably at least 70%, and most preferably at least 90% of the biological activity of the intact proteins. Analogs refer to species and allelic variants of the intact protein, or amino acid replacements, insertions or deletions thereof that have at least 30%, more preferably at least 70%, and most preferably 90% of the biological activity of the intact protein.

Figure 2:
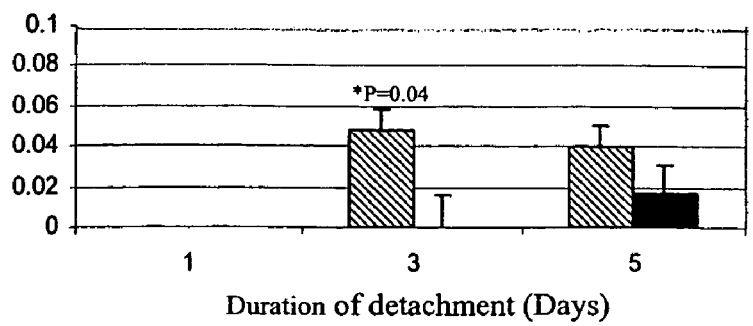
FIG. 2 depicts a bar chart showing the ratio of cleaved caspase 3 to pro-caspase 3 in densitometry units in detached retinas (hatched bars) and attached retinas (solid bars) at one, three and five days post retinal detachment.

With reference to the foregoing proteins, the term "analogs" includes variant sequences that are at least 80% similar or 70% identical, more preferably at least 90% similar or 80% identical, and most preferably 95% similar or 90% identical to at least a portion of one of the exemplary proteins described herein, for example, Brain Derived Growth Factor. To determine whether a candidate protein has the requisite percentage similarity or identity to a reference polypeptide, the candidate amino acid sequence and the reference amino acid sequence are first aligned using the dynamic programming algorithm described in Smith and Waterman (1981) J. MOL BIOL. 147: 195-197, in combination with the BLOSUM62 substitution matrix described in FIG. 2 of Henikoff and Henikoff (1992), PROC. NAT. ACAD. SCI. USA 89:10915-10919. An appropriate value for the gap insertion penalty is −12, and an appropriate value for the gap extension penalty is −4. Computer programs performing alignments using the algorithm of Smith-Waterman and the BLOSUM62 matrix, such as the GCG program suite (Oxford Molecular Group, Oxford, England), are commercially available and widely used by those skilled in the art. Once the alignment between the candidate and reference sequence is made, a percent similarity score may be calculated. The individual amino acids of each sequence are compared sequentially according to their similarity to each other. If the value in the BLOSUM62 matrix corresponding to the two aligned amino acids is zero or a negative number, the pairwise similarity score is zero; otherwise the pairwise similarity score is 1.0. The raw similarity score is the sum of the pairwise similarity scores of the aligned amino acids. The raw score is then normalized by dividing it by the number of amino acids in the smaller of the candidate or reference sequences. The normalized raw score is the percent similarity. Alternatively, to calculate a percent identity, the aligned amino acids of each sequence are again compared sequentially. If the amino acids are non-identical, the pairwise identity score is zero; otherwise the pairwise identity score is 1.0. The raw identity score is the sum of the identical aligned amino acids. The raw score is then normalized by dividing it by the number of amino acids in the smaller of the candidate or reference sequences. The normalized raw score is the percent identity. Insertions and deletions are ignored for the purposes of calculating percent similarity and identity. Accordingly, gap penalties are not used in this calculation, although they are used in the initial alignment.

Under certain circumstances, it may be advantageous to also administer to the individual undergoing treatment with the apoptosis inhibitor an anti-permeability agent and/or an anti-inflammatory agent so as to minimize photoreceptor cell death. An anti-permeability agent is a molecule that reduces the permeability of normal blood vessels. Examples of such molecules include molecules that prevent or reduce the expression of genes encoding, for example, Vascular Endothelial Growth Factor (VEGF) or an Intercellular Adhesion Molecule (ICAM) (for example, ICAM-1, ICAM-2 or ICAM-3). Exemplary molecules include antisense oligonucleotides and antisense peptidyl nucleic acids that hybridize in vivo to a nucleic acid encoding a VEGF gene, an ICAM gene, or a regulatory element associated therewith. Other suitable molecules bind to and/or reduce the activity of, for example, the VEGF and ICAM molecules (for example, anti-VEGF and anti-ICAM antibodies and antigen binding fragments thereof, and anti-VEGF or anti-ICAM aptamers). Other suitable molecules bind to and prevent ligand binding and/or activation of a cognate receptor, for example, the VEGF receptor or the ICAM receptor. Such molecules may be administered to the individual in an amount sufficient to reduce the permeability of blood vessels in the eye. An anti-inflammatory agent is a molecule that prevents or reduces an inflammatory response in the eye. Exemplary anti-inflammatory agents include steroids, for example, hydrocortisone, dexamethasone sodium phosphate, methylpredisolone, and triamcinolone acetonide. Such molecules may be administered to the individual in an amount sufficient to reduce or eliminate an inflammatory response in the eye.

As a result, the invention provides an improved method for treating a retinal detachment. The method involves administering an apoptosis inhibitor before and/or during and/or after surgical reattachment of the detached retina. The apoptosis inhibitor may be administered to the mammal from the time the retinal detachment is detected to the time the retina is repaired, for example, via surgical reattachment. It is understood, however, that under certain circumstances, it may be advantageous to administer the apoptosis inhibitor to the mammal even after the retina has been surgically repaired. For example, even after the surgical reattachment of a detached retina in patients with rhegmatogenous retinal detachments, persistent subretinal fluid may exist under the fovea as detected by ocular coherence tomography long after the surgery has been performed (see, Hagimura et al. (2002) AM. J. OPHTHALMOL. 133:516-520). As a result, even after surgical repair the retina may still not be completely reattached to the underlying retinal pigment epithelium and choroid. Furthermore, when retinal detachments occur secondary to another disorder, for example, the neovascular form of age-related macular degeneration and ocular melanomas, it may be beneficial to administer the neuroprotective agent to the individual while the underlying disorder is being treated so as to minimize loss of photoreceptor cell viability. Accordingly, in such cases, it may be advantageous to administer the apoptosis inhibitor to the mammal for one week, two weeks, three weeks, one month, three months, six months, nine months, one year, two years or more (i) after retinal detachment has been identified, and/or (ii) after surgical reattachment of the retina has occurred, and/or (iii) after detection of an underlying degenerative disorder, so as to minimize photoreceptor cell death.

Once the appropriate apoptosis inhibitors have been identified, they may be administered to the mammal of interest in any one of a wide variety of ways. It is contemplated that an apoptosis inhibitor, for example, a caspase inhibitor, can be administered either alone or in combination with a neuroprotective agent, for example, a neurotrophic agent. It is contemplated that the efficacy of the treatment may be enhanced by administering two, three, four or more different agents either together or one after the other. Although the best means of administering a particular apoptosis inhibitor or combination of an apoptosis inhibitor with another neuroprotective agent may be determined empirically, it is contemplated that the active molecules may be administered locally or systemically.

Systemic modes of administration include both oral and parenteral routes. Parenteral routes include, for example, intravenous, intrarterial, intramuscular, intradermal, subcutaneous, intranasal and intraperitoneal routes. It is contemplated that the apoptosis inhibitors administered systemically may be modified or formulated to target the apoptosis inhibitor to the eye. Local modes of administration include, for example, intraocular, intraorbital, subconjuctival, intravitreal, subretinal or transcleral routes. It is noted, however, that local routes of administration are preferred over systemic routes because significantly smaller amounts of the apoptosis inhibitor can exert an effect when administered locally (for example, intravitreally) versus when administered systemically (for example, intravenously). Furthermore, the local modes of administration can reduce or eliminate the incidence of potentially toxic side effects that may occur when therapeutically effective amounts of an apoptosis inhibitor (i.e., an amount of an apoptosis inhibitor sufficient to reduce, minimize or eliminate the death of photoreceptor cells following retinal detachment) are administered systemically.

Administration may be provided as a periodic bolus (for example, intravenously or intravitreally) or as continuous infusion from an internal reservoir (for example, from an implant disposed at an intra- or extra-ocular location (see, U.S. Pat. Nos. 5,443,505 and 5,766,242)) or from an external reservoir (for example, from an intravenous bag). The apoptosis inhibitor may be administered locally, for example, by continuous release from a sustained release drug delivery device immobilized to an inner wall of the eye or via targeted transscleral controlled release into the choroid (see, for example, PCT/US00/00207, PCT/US02/14279, Ambati et al. (2000) INVEST. OPHTHALMOL. VIS. SCI.41:1181-1185, and Ambati et al. (2000) INVEST. OPHTHALMOL. VIS. SCI.41:1186-1191). A variety of devices suitable for administering an apoptosis inhibitor locally to the inside of the eye are known in the art. See, for example, U.S. Pat. Nos. 6,251,090, 6,299,895, 6,416,777, 6,413,540, and 6,375,972, and PCT/US00/28187.

The apoptosis inhibitor also may be administered in a pharmaceutically acceptable carrier or vehicle so that administration does not otherwise adversely affect the recipient's electrolyte and/or volume balance. The carrier may comprise, for example, physiologic saline or other buffer system.

In addition, it is contemplated that the apoptosis inhibitor may be formulated so as to permit release of the apoptosis inhibitor over a prolonged period of time. A release system can include a matrix of a biodegradable material or a material which releases the incorporated apoptosis inhibitor by diffusion. The apoptosis inhibitor can be homogeneously or heterogeneously distributed within the release system. A variety of release systems may be useful in the practice of the invention, however, the choice of the appropriate system will depend upon rate of release required by a particular drug regime. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that apoptosis inhibitor having different molecular weights are released by diffusion through or degradation of the material.

Representative synthetic, biodegradable polymers include, for example: polyamides such as poly(amino acids) and poly (peptides); polyesters such as poly(lactic acid), poly(glycolic acid), poly(lactic-co-glycolic acid), and poly(caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly(ethylene oxide), poly (ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

One of the primary vehicles currently being developed for the delivery of ocular pharmacological agents is the poly (lactide-co-glycolide) microsphere for intraocular injection. The microspheres are composed of a polymer of lactic acid and glycolic acid, which are structured to form hollow spheres. These spheres can be approximately 15-30 μm in diameter and can be loaded with a variety of compounds varying in size from simple molecules to high molecular weight proteins such as antibodies. The biocompatibility of these microspheres is well established (see, Sintzel et al. (1996) EUR. J. PHARM. BIOPHARM. 42: 358-372), and microspheres have been used to deliver a wide variety of pharmacological agents in numerous biological systems. After injection, poly(lactide-co-glycolide) microspheres are hydrolyzed by the surrounding tissues, which cause the release of the contents of the microspheres (Zhu et al. (2000) NAT. BIOTECH. 18: 52-57). As will be appreciated, the in vivo half-life of a microsphere can be adjusted depending on the specific needs of the system.

The type and amount of apoptosis inhibitor administered may depend upon various factors including, for example, the age, weight, gender, and health of the individual to be treated, as well as the type and/or severity of the retinal detachment to be treated. As with the modes of administration, it is contemplated, that the optimal apoptosis inhibitors and dosages of those apoptosis inhibitors may be determined empirically. The apoptosis inhibitor preferably is administered in an amount and for a time sufficient to permit the survival of at least 25%, more preferably at least 50%, and most preferably at least 75%, of the photoreceptor cells in the detached region of the retina.

By way of example, protein-, peptide- or nucleic acid-based apoptosis inhibitors can be administered at doses ranging, for example, from about 0.001 to about 500 mg/kg, optionally from about 0.01 to about 250 mg/kg, and optionally from about 0.1 to about 100 mg/kg. Nucleic acid-based apoptosis inhibitors may be administered at doses ranging from about 1 to about 20 mg/kg daily. Furthermore, antibodies may be administered intravenously at doses ranging from about 0.1 to about 5 mg/kg once every two to four weeks. With regard to intravitreal administration, the apoptosis inhibitors, for example, antibodies, may be administered periodically as boluses in dosages ranging from about 10 μg to about 5 mg/eye, and optionally from about 100 μg to about 2 mg/eye. With regard to transcleral administration, the apoptosis inhibitors, may be administered periodically as boluses in dosages ranging from about 0.1 μg to about 1 mg/eye, and optionally from about 0.5 μg to about 0.5 mg/eye.

The present invention, therefore, includes the use of a apoptosis inhibitor, for example, a caspase inhibitor, in the preparation of a medicament for treating an ocular condition associated with a retinal detachment, for example, a loss of vision as a result of photoreceptor cell death in the region of retinal detachment. A composition comprising one or more apoptosis inhibitors, one agent optionally being a caspase inhibitor, may be provided for use in the present invention. The apoptosis inhibitor or agents may be provided in a kit which optionally may comprise a package insert with instructions for how to treat the patient with the retinal detachment. For each administration, the apoptosis inhibitor may be provided in unit-dosage or multiple-dosage form. Preferred dosages of the apoptosis inhibitors, however, are as described above.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

In light of the foregoing description, the specific non-limiting examples presented below are for illustrative purposes and are not intended to limit the scope of the invention in any way.

EXAMPLES

Example 1

Detection of Caspase Activity Following Retinal Detachment

This example demonstrates that certain caspases, particularly caspases 3, 7 and 9, are activated in photoreceptor cells following retinal detachment. The example also demonstrates that photoreceptor death is mediated by the intrinsic apoptotic pathway following retinal detachment.

Experimental retinal detachments were created using modifications of previously published protocols (Cook et al. (1995) INVEST. OPHTHALMOL. VIS. SCI. 36(6):990-6; Hisatomi et al. (2001) AM. J. PATH. 158(4):1271-8). Briefly, rats were anesthetized using a 50:50 mixture of ketamine (100 mg/ml) and xylazine (20 mg/ml). Pupils were dilated using a topically applied mixture of phenylephrine (5.0%) and tropicamide (0.8%). A 20 gauge micro-vitreoretinal blade was used to create a sclerotomy approximately 2 mm posterior to the limbus. Care was taken not to damage the lens during the sclerotomy procedure. A Glaser subretinal injector (20 gauge shaft with a 32 gauge tip, Becton-Dickinson, Franklin Lakes, N.J.) connected to a syringe filled with 10 mg/ml of sodium hyaluronate (Healon®, Pharmacia and Upjohn Company, Kalamazoo, Mich.) then was introduced into the vitreous cavity. The tip of the subretinal injector was used to create a retinotomy in the peripheral retina, and then the Healon was slowly injected into the subretinal space to elevate the retina from the underlying retinal pigment epithelium. Retinal detachments were created only in the left eye (OS) of each animal, with the right eye (OD) serving as the control. In each experimental eye, approximately one half of the retina was detached, allowing the attached portion to serve as a further control.

Following creation of the experimental retinal detachment, intraocular pressures were measured before and immediately after retinal detachment with a Tono-pen. No differences in intraocular pressures were noted. The retinal break created by the subretinal injector was confined only to the site of the injection.

Light microscopic analysis of the detached retinas showed an increase in morphologic stigmata of apoptosis as a function of time after detachment. Eyes then were enucleated one, three, five and seven days after creation of the retinal detachment. For light microscopic analysis, the cornea and lens were removed and the remaining eyecup placed in a fixative containing 2.5% glutaraldehyde and 2% formaldehyde in 0.1M cacodylate buffer (pH 7.4) and stored at 4° C. overnight. Tissue samples then were post-fixed in 2% osmium tetroxide, dehydrated in graded ethanol, and embedded in epoxy resin. One-micron sections were stained with 0.5% toluidine blue in 0.1% borate buffer and examined with a Zeiss photomicroscope (Axiophot, Oberkochen, Germany).

At one day after creation of the detachment, pyknosis in the outer nuclear layer was confined to the area of the peripheral retinotomy site through which the subretinal injector was introduced. By three days, however, pyknotic nuclei were seen in the whole outer nuclear layer of the retina in the area of the detachment. Extrusion of pyknotic nuclei from the outer nuclear layer into the subretinal space were observed. The remaining layers of the retina appeared morphologically normal. No inflammatory cells were seen, and there was no apparent disruption of the retinal vasculature. Similar changes were seen in sections from retinas detached for up to one week. No pyknotic nuclei were seen in the area of the attached retina or in the fellow, non-detached eye. The amount of outer nuclear layer pyknosis was similar between detachments of three-day or one week duration.

Disruption of the photoreceptor outer segments was a prominent feature in the detached retinas. Outer segments of the control eyes and the attached portions of the experimental eyes had an orderly, parallel arrangement. Detachments produced artifactually during tissue processing in these eyes did not alter the photoreceptor morphology. In contrast, the photoreceptor outer segments of detached retinas were severely disorganized and lost their normal structural organization. Additionally, outer segments in attached areas had similar lengths, whereas the outer segments in detached areas showed variable lengths.

Internucleosomal DNA cleavage in photoreceptor cells was detected via TUNEL staining. For TUNEL staining, the cornea and lens were not removed after enucleation, but rather the whole eye was fixated overnight at 4° C. in a phosphate buffered saline solution of 4% paraformaldehyde solution (pH 7.4). Then, a section was removed from the superior aspect of the globe and the remaining eyecup embedded in paraffin and sectioned at a thickness of 6 µm. TUNEL staining was performed on these sections using the TdT-Fragel DNA Fragmentation Detection Kit (Oncogene Sciences, Boston, Mass.) in accordance with the manufacturer's instructions. Reaction signals were amplified using a pre-formed avidin: biotinylated-enzyme complex (ABC-kit, Vector Laboratories, Burlingame, Calif.). Internucleosomally cleaved DNA fragments were stained with diaminobenzidine (DAB) (staining indicates TUNEL positive cells) and sections were then counterstained with methylene green.

TUNEL-positive cells were detected at all time points tested (one, three, five and seven days post-detachment). TUNEL-positive staining was confined only to the photoreceptor cell layer. Two eyes with retinal detachments that persisted for two months were monitored. The TUNEL assay at two months did not reveal any staining indicating the presence of internucleosomally cleaved DNA. The prolonged detachment was associated with a marked reduction in the thickness of and number of cell bodies contained in the outer nuclear layer as compared to the non-detached retina.

Antibodies specific for caspases 3, 7, 9 and PARP were used in Western blots to probe total retinal protein extracts at various times after creation of the retinal detachment. For Western blot analysis, retinas from both experimental and control eyes were manually separated from the underlying retinal pigment epithelium/choroid at days one, three and five after creation of the retinal detachment. In eyes with retinal detachments, the experimentally detached portion of the retina was separated from the attached portion of the retina and analyzed separately. Retinas were homogenized and lysed with buffer containing 1 mM ethylene diaminetetraacetic acid/ethylene glycol-bis (2-aminoethylethel-N,N, N',N'-tetraacetic acid/dithiothreitol, 10 mM HEPES pH 7.6, 0.5% (octylphenoxy)polyethoxyethanol (IGEPAL), 42 mM potassium chloride, 5 mM magnesium chloride, 1 mM phenyl-methanesulfonyl fluoride and 1 tablet of protease inhibitors per 10 ml buffer (Complete Mini, Roche Diagnostics GmbH, Mannheim, Germany). Samples were incubated for 15 minutes on ice, and then centrifuged at 21,000 rpm at 4° C. for 30 min. The protein concentration of the supernatant was determined using the Bio-Rad Dc Protein Assay reagents (Bio-Rad Laboratories, Hercules, Calif.). Proteins were separated via sodium dodecyl sulfate-polyacrylamide gel electrophoresis (7.5% and 15% Tris-HCL Ready-Gels, Bio-Rad Laboratories), in which 30 µg of total retinal protein were applied in each lane. The fractionated proteins were transferred to a PVDF membrane (Immobilon-P, Millipore, Bedford, Mass.). The resulting membrane was blocked with 5% non-fat dry milk in 0.1% TBST IGEPAL. The blocked membranes then were incubated with antibodies against caspase 7 (1:1,000; Cell Signaling Technology, Beverly, Mass.), caspase 9 (1:1, 000; Medical & Biological Laboratories, Naka-ku Nagoya, Japan), cleaved-caspase 3 (1:1,000; Cell Signaling Technology, Beverly, Mass.), caspase 3 (1:2000; Santa Cruz, Santa Cruz, Calif.) or PARP (1:1000; Cell Signaling Technologies, Beverly, Mass.) overnight at 4° C. Bands were detected using the ECL-Plus reagent (Amersham, Pharmacia, Piscataway, N.J.). Membranes were exposed to HyperFilm (Amersham) and densitometry was preformed using ImageQuant 1.2 software (Molecular Dynamics, Inc., Sunnyvale, Calif.). For each eye tested, densitometry levels were normalized by calculating the ratio of the cleaved-form to the pro-form of the protein of interest. Pro-caspase 7 levels were normalized to the densitometry readings from a non-specific band detected by the secondary IgG. Five eyes were used for each time point, except for the PARP levels for day 5 after detachment for which only four eyes were used. All statistical comparisons were performed using a paired t-test.

The cleaved, or active form of caspase 3 was elevated in the detached retinas as compared to the attached retinas. The level of cleaved-caspase 3 increased as a function of time after detachment, with a peak at approximately three days (see, FIG. 2). No cleaved-caspase 3 was detected in the control eye or in the attached portion of the retina in the experimental eye.

Figure 3:
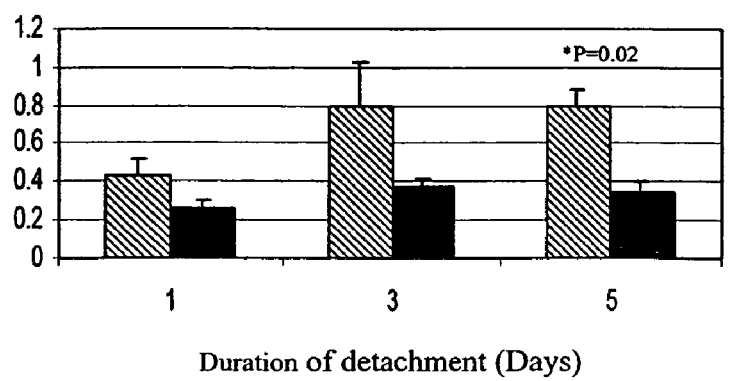
FIG. 3 depicts a bar chart showing the ratio of cleaved caspase 9 to pro-caspase 9 in densitometry units in detached retinas (hatched bars) and attached retinas (solid bars) at one, three and five days post retinal detachment.
Figure 4:
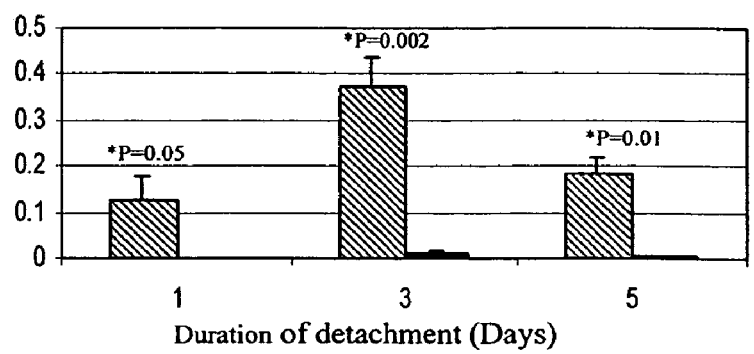
FIG. 4 depicts a bar chart showing the level of caspase 7 in densitometry units in detached retinas (hatched bars) and attached retinas (solid bars) at one, three and five days post retinal detachment.
Figure 5:
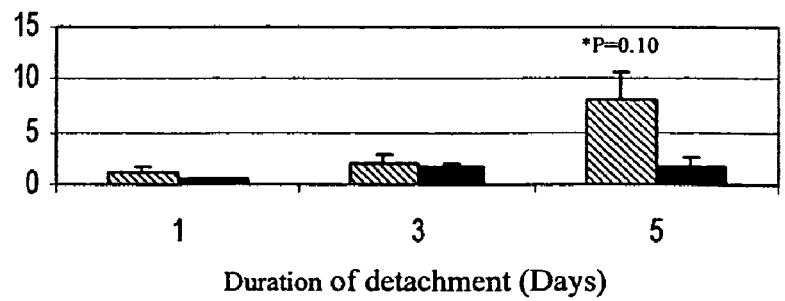
FIG. 5 depicts a bar chart showing the ratio of cleaved poly-ADP ribose-polymerase (PARP) to pro-PARP in densitometry units in detached retinas (hatched bars) and attached retinas (solid bars) at one, three and five days post retinal detachment

The ratio of the active to inactive form of caspase 9 also increased as a function of time after creation of the experimental retinal detachment (see, FIG. 3). The peak level of cleaved-caspase 9 was seen at three to five days after creation of the detachment. The caspase 7 antibody was able only to detect the pro-form of the protein. There was, however, a significant difference in the amount of the pro-form detected in the protein extract from the detached retinas as compared to the attached retinas (see, FIG. 4). Western blotting with antibodies against PARP (a component of the apoptosis cascade downstream of caspase 7) detected an increase in the level of cleaved-PARP that was maximal at five days after detachment (see, FIG. 5). P-values for the comparisons between detached and attached retinas are shown in FIGS. 2-5.

The results demonstrate that caspase 3, caspase 7 and caspase 9 are all activated in photoreceptor cells following retinal attachment.

Example 2

Activation of FAS-mediated Apoptotic Pathway in the Retina Following Retinal Detachment The purpose of this example was to determine whether only the intrinsic pathway becomes activated during retinal detachment, or whether the receptor-mediated pathway also contributes to photoreceptor death.

Experimental retinal detachments were created in Brown-Norway rats by injecting 10% hyaluronic acid into the subretinal space. Retinal tissue was harvested at 2, 4, 8, 24, 72 and 168 hours after creation of the detachment. Immunoprecipitation was performed to assess for FAS-receptor/FAS-ligand complex formation, and activation of caspase 8 and BID was assessed by Western blot analysis. Caspase 9 activity assay and immunoprecipitation of the caspase 9/cytochrome C complex was performed at these same time points. The results demonstrate that the FAS-mediated apoptotic pathway is activated during retinal detachment, and that FAS pathway activation precedes that of intrinsic pathway.

2.1. Animal Model

The experiments described in Examples 2-4 were performed in accordance with the ARVO Statement for the Use of Animals in Ophthalmic and Vision Research and the guidelines established by the University Committee on Use and Care of Animals of the University of Michigan. Retinal detachments were created in adult male Brown-Norway rats (300-400 gm) essentially as described in Example 1 but with minor modifications.

Briefly, rats were anesthetized with a 50:50 mix of ketamine (100 mg/ml) and xylazine (20 mg/ml), and pupils were dilated with topical phenylephrine (2.5%) and tropicamide (1%). A sclerotomy was created approximately 2 mm posterior to the limbus with a 20-guage microvitreoretinal blade (Walcott Scientific, Marmora, N.J.), with special caution to not damage the lens. A Glaser subretinal injector (32-gauge tip; BD Ophthalmic Systems, Sarasota, Fla.) connected to a syringe filled with 10 mg/ml sodium hyaluronate (Healon®; Pharmacia and Upjohn Co., Kalamazoo, Mich.) was introduced through the sclerotomy into the vitreous cavity. The tip of the subretinal injector was introduced into the subretinal space through a peripheral retinotomy, and the sodium hyaluronate was slowly injected. The neurosensory retina was thus detached from the underlying retinal pigment epithelium. In all experiments, approximately one-third to one-half of the retina was detached. Detachments were made in the left eye, with the right eye serving as the control. For control eyes, a sham surgery was performed in which all components of the procedure were performed except introduction of the subretinal injector and creation of the detachment. In experimental eyes, only the detached portion of the retina was harvested for analysis.

2.2. Western Blot Analysis

Retinas from experimental and control eyes were dissected from the RPE-choroid at 3 and 7 days after retinal detachment. Retinas were homogenized and lysed with buffer containing 10 mM HEPES (pH 7.6), 0.5% IGEPAL, 42 mM KCL, 1 mM PMSF, 1 mM EDTA, 1 mM EGTA, 1 mM DTT, 5 mM $MgCL_2$, and 1 tablet of protease inhibitors per 10 mL buffer (Complete Mini; Roche Diagnostics GmbH, Mannheim, Germany). The homogenates were incubated on ice and centrifuged at 22,000 g at 4° C. for 60 minutes. The protein concentration of the supernatant was determined using the Dc Protein Assay kit (Bio-Rad Laboratories; Hercules Calif.). The protein samples were loaded and run on SDS-Polyacrylamide gels (4-20% Tris-HCL ready gels, Bio-Rad Laboratories). After electrophoretic separation the proteins were transferred onto polyvinylidene fluoride (PVDF) membranes (Immobilon-P). Protein bands were visualized with Ponceau S staining and the lanes assessed for equal loading by densitometry on a non-specific band present across all lanes. Membranes were then placed in 5% nonfat powdered milk in TBS (150 mM NaCl, 50 mM Tris; pH 7.6) and incubated overnight at 4° C. on a shaker. Membranes were then incubated with the primary antibody in 2.5% powdered milk in TBS for overnight at 4° C. Membranes were washed extensively with TBS-T (0.1% Tween 20), and then incubated with horseradish peroxidase labeled secondary antibody (1:3000, Santa Cruz Biotechnology) for 1 hour at room temperature. Bands were visualized with ECL-Plus (Amersham, Piscataway, N.J.) according to the manufacturer's instructions. Antibodies against the following proteins were used: caspase-8 (1:800 dilution, Santa Cruz Biotechnology, Santa Cruz, Calif.), caspase-9 (1:2000 dilution, MBL, Nakaku, Japan), cytochrome C (1:1000 dilution, BD Biosciences, San Jose, Calif.), BID (1:1000 dilution, Santa Cruz Biotechnology), FAS (1:1000 dilution, Santa Cruz Biotechnology), and FAS-ligand (1:2000 dilution, MBL).

2.3. Immunoprecipitation

Retinal samples were isolated as described in Section 2.2. For each condition tested, 20 µg of protein extract was placed in 100 µl of immunoprecipitation buffer-A (IP-A)+PMSF (20 mM Tris pH 7.5, 100 mM NaCl, 1 mM EDTA, 1 mM phenylmethylsulfonyl fluoride) and 100 µl of IP-B buffer (100 mM Tris pH 7.5, 100 mM NaCl, 0.4% Triton X-100). Samples were first incubated overnight with an anti-FAS antibody (0.2 µg anti-FAS rabbit polyclonal IgG (Santa Cruz, sc-716)) at 4° C. with gentle rocking, then incubated for 2 hours in 35 µl of 50% suspension of protein G sepharose beads at 4° C. with gentle rocking. Beads were prewashed 4 times with 1 ml of cold IP-C buffer (50 mM tris pH 7.5, 100 mM NaCl, 0.2% Triton X-100), then pelleted at 2200 rpm for 6 minutes. Resuspended beads with attached proteins were diluted with Laemmli Dye loading buffer and heated at 95° C. for 10 minutes prior to running on a 4-20% SDS-PAGE ready gel (Bio-Rad). Western blot analysis was performed as described above using a monoclonal antibody against FAS-Ligand (MBL, D057-3). Immunoprecipitation of the caspase 9/cytochrome C complex was performed using a similar protocol, except the antibodies used were anti-caspase 9 (rabbit polyclonal IgG (Santa Cruz, sc-7885)) and a monoclonal antibody against cytochrome C (MBL, BV-3026-3). Densitometry of Western blot bands was performed using a Kodak 440CF Image Station (Kodak Company, Rochester, N.Y.). For each time point, the densitometry reading of the detached retina was normalized against the densitometry reading of attached retina at the same time point.

2.4. Caspase 9 Activity Assay

Caspase 9 activity was measured using a calorimetric tetrapeptide LEHD-pNA cleavage assay kit according to the manufacturer's instructions (BioVision, Mountain View, Calif.). In this assay, 100 µg of total retinal protein from either attached or detached retinas were incubated with substrate (LEHD-pNA, 200 µM final concentration) at 37° C. for 60 min. Absorbance was measured at 405 nm in a microplate reader (SpectraMAX 190, Molecular Devices). As a negative control, retinal protein was incubated with assay buffer lacking any tetrapeptide. A second negative control was used in which assay buffer alone was incubated with the tetrapeptide. As a positive control, purified caspase 9 was incubated with the tetrapeptide alone. For each time point, the caspase 9 activity in the detached retina was normalized against the caspase 9 activity in attached retina at the same time point.

2.5. Results

Figure 6:
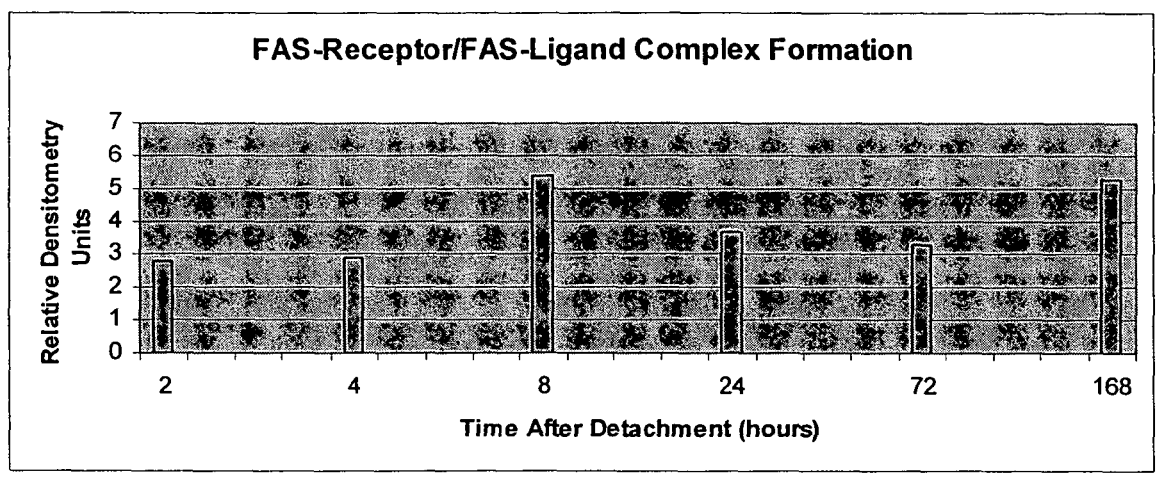
FIG. 6 depicts a bar chart showing the kinetics of FAS-receptor/FAS-ligand complex formation as a function of time after retinal detachment (the units on the ordinate axis correspond to normalized densitometry readings of immunoprecipitated complexes)

The initial experiment determined whether or not the FAS pathway becomes activated upon retinal detachment. Immunoprecipitation studies demonstrated that the receptor/FAS-ligand complex is formed upon retinal detachment (data not shown). Activation of caspase 8 and BID was demonstrated on Western blot analysis by formation of their cleaved forms, as would be expected by the formation of functional FAS-receptor/FAS-ligand complex. The peak of FAS-receptor/FAS-ligand complex formation occurred 8 hours after retinal detachment (see, FIG. 6). This preceded the peak of caspase 9 activity, which occurred 24 hours after creation of the detachment (see, FIG. 7a), which corresponded to the peak of caspase 9/cytochrome C complex formation (see, FIG. 7b). Normalizing the densitometry readings for any decrease in outer nuclear layer thickness that might result from the retinal detachment did not significantly alter the relative values shown.

These experiments demonstrate that retinal detachment up regulates and activates the FAS/FAS-ligand pathway. This up regulation occurs at the transcription level, as demonstrated by the increased levels of messenger RNA (data not shown). These components are not just present at increased levels of pro-form, but become activated by the detachment as evidenced by their cleavage into enzymatically active states. The data also shows that FAS activation precedes that of the intrinsic pathway, when taken in conjunction with the ability to decrease the latter's activity by inhibition of the former suggests a direct linkage of activation between the two.

Example 3

Modulation of Caspase 9 and FAS Receptor Activity Following Retinal Detachment

This Example demonstrates that it is possible to module the activity of caspase 9 in vivo following retinal detachment. Direct inhibition of the intrinsic pathway was performed using the caspase 9 inhibitor z-Leu-Glu-His-Asp-fluoromethylketone (zLEHD.fmk). Indirect inhibition (via inhibition of FAS complex formation) was performed using neutralizing antibodies against either the FAS-receptor or FAS-ligand. Injection of zLEHD.fmk into the subretinal space of a detached retina resulted in decreased caspase 9 activity, as did injection of anti-FAS-receptor antibody into either the subretinal space or intravitreally.

In these experiments the retina was detached with sodium hyaluronate according to the protocol described in Example 2, followed immediately by the injection of 5 µl of inhibitor. In one experiment, the direct inhibitor of caspase 9-zLEHD.fmk was tested. Five microliters of the zLEHD.fmk (2 mM solution in DMSO) (BioVision) was injected into the subretinal space of the detached retina using a Hamilton Syringe (Hamilton Corp, Reno, Nev.). Five microliters of DMSO was injected into the subretinal space of the detached retinas as a control for the solvent in which the zLEHD.fmk was dissolved. In another experiment, the neutralizing antibody against the FAS-receptor (5 µg in phosphate buffered saline) (clone ZB4, Upstate, Lake Placid, N.Y.) or FAS-ligand (5 µg in phosphate buffered saline) (clone NOK-1, BD-Biosciences) was injected either into the subretinal space or the vitreous cavity.

In all inhibition experiments, the retinas were harvested at 24 hours after detachment, as this was the peak of caspase 9 activity seen after detachment (as shown in Example 2). The caspase 9 activity in the detached retina was normalized against the caspase 9 activity in attached retina at the same time point.

Figures 7A, 7B:
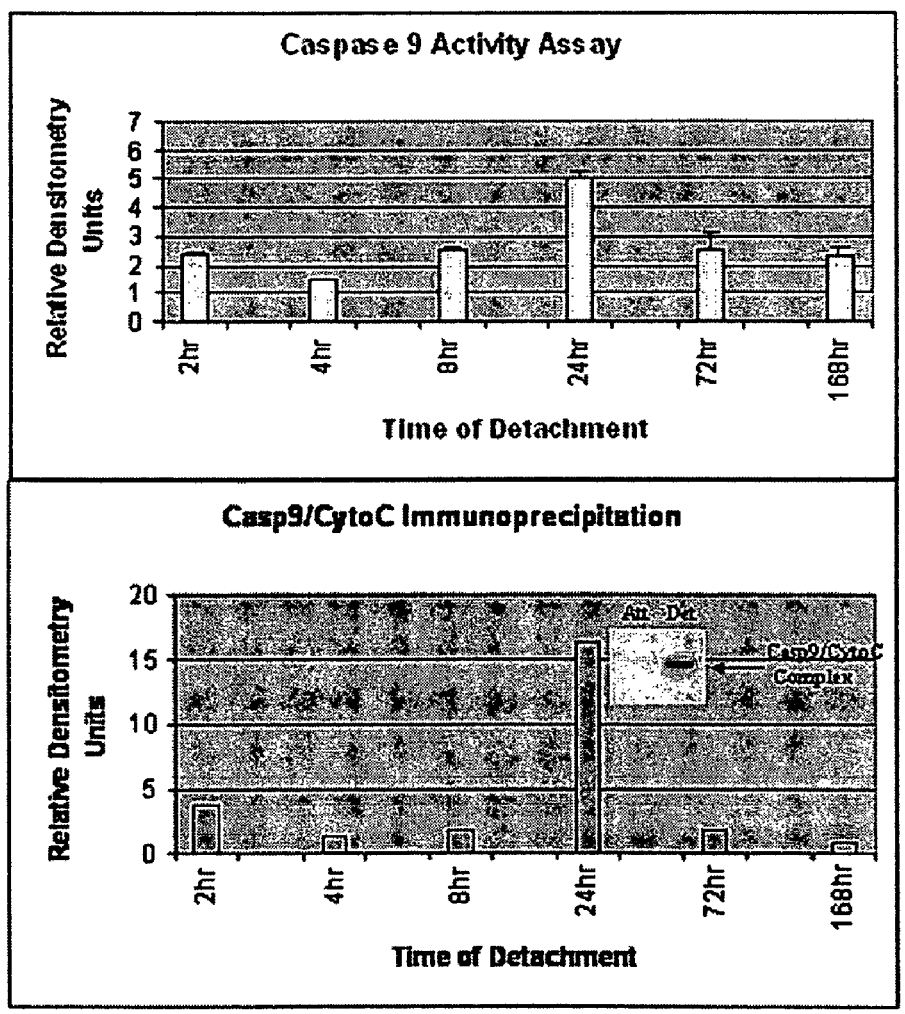
FIGS. 7a and 7b depict bar charts showing the kinetics of intrinsic pathway activation as measured by caspase 9 activity levels as a function of time after retinal detachment (FIG. 7a) and by caspase 9/cytochrome C complex formation as a function of time after retinal detachment (FIG. 7b)
Figure 8:
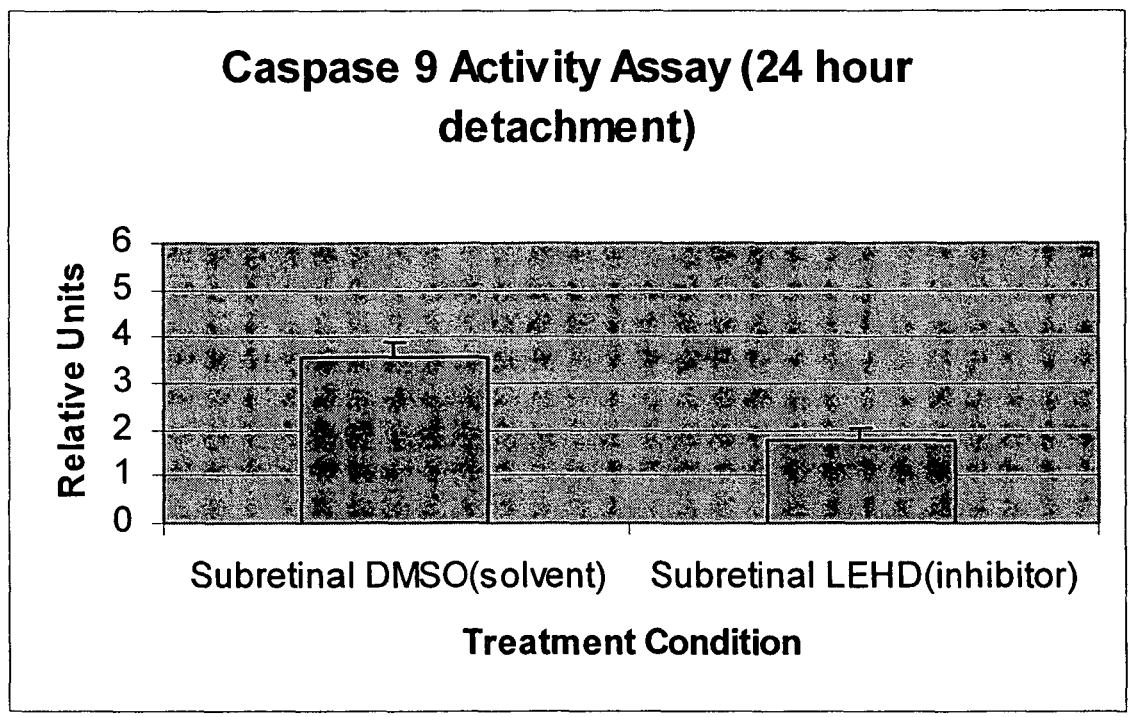
FIG. 8 depicts a bar chart showing the inhibition of caspase 9 activity 24 hours after retinal detachment, as measured in vitro, following injection of either DMSO solvent alone or DMSO solvent containing the caspase 9 inhibitor zLEHD.fmk at the time of detachment.

Caspase 9 activity levels were used as a measurement of intrinsic pathway activation. The activity levels were tested 24 hours after the retinal detachment was created and inhibitor applied, as this was the time of peak caspase 9 activity (FIG. 7a). Injection of the caspase 9 inhibitor zLEHD.fmk into the subretinal space of a detached retina significantly reduced caspase 9 activity to approximately 50% of the control level ($p=0.05$) (FIG. 8).

Figure 9:
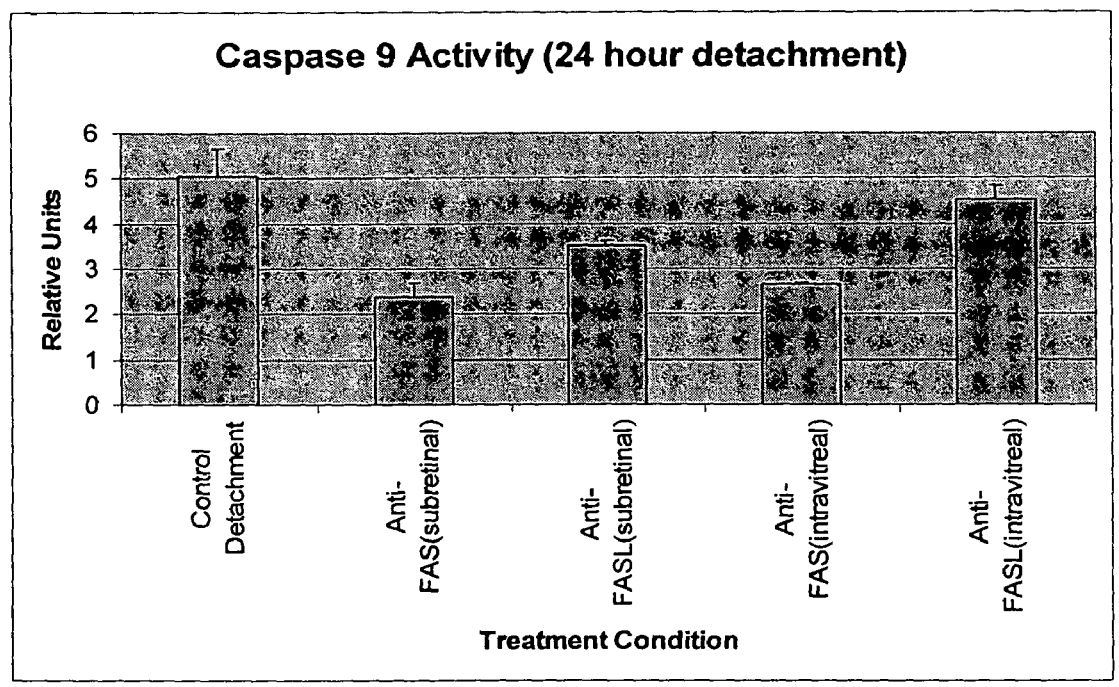
FIG. 9 depicts a bar chart showing the inhibition of caspase 9 activity 24 hours after retinal detachment, as measured in vitro, following injection of anti-FAS-receptor (anti-FAS) neutralizing antibody, or anti-FAS-ligand (anti-FASL) neutralizing antibody at the time of detachment.

Injection of neutralizing antibodies against either the FAS-receptor or the FAS-ligand into the subretinal space of the detached retina also resulted in the reduction of caspase 9 activity by approximately 50% ($p=0.05$) (FIG. 9). The effect of intravitreal injection of these antibodies was less than that seen with a subretinal injection, and did not reach statistical significance. Intravitreally injected anti-FAS-receptor antibody reduced caspase 9 activity by only about 30% ($p=0.13$). Intravitreal injection of anti-FAS-ligand antibody resulted in only a 10% reduction of caspase 9 activity ($p=0.54$).

Example 4

Preservation of Photoreceptor Viability Following Retinal Detachment

This example demonstrates that administration of an apoptosis inhibitor can preserve photoreceptor cells following retinal detachment. The administration of a caspase 9 inhibitor reduced the number of apoptotic cells following retinal detachment.

Briefly, the retinal detachments were created in the left eyes of three Brown Norway rats, as described in Example 2, section 2.1. The detachment was located on the temporal portion of the retina, and comprised approximately one third of the total retinal area.

A first rat received the retinal detachment only. A second rat received the retinal detachment and a caspase 9 inhibitor in DMSO. Briefly, immediately after the retina was detached, 5 µl of the zLEHD.fmk (2 mM solution in DMSO) (BioVision) was injected into the subretinal space of the detached retina using a Hamilton Syringe (Hamilton Corp, Reno, Nev.). A third rat received the retinal detachment and DMSO (solvent control). Briefly, 5 µl of DMSO was injected into the subretinal space of the detached retinas as a control for the solvent in which the zLEHD.fmk was dissolved.

The rats were allowed to recover from the surgery and were returned to their cages, as per standard animal care protocols. Seventy-two hours (3 days) after creation of the detachments, the eyes were enucleated and immersion-fixed in 4% paraformaldehyde solution for 24 hours. The fixed eyes were then embedded in paraffin and sectioned for histologic analysis. TUNEL staining was performed on the sections using a commercially-available kit (TdT-Fragel DNA Fragmentation Detection Kit: Oncogene, Boston, Mass.) according to the manufacturer's instructions.

The number of TUNEL-positive cells/100 cells in the outer nuclear layer were counted for 3 high power fields per section for 2 separate slides. The results are summarized in Table 1.

TABLE 1

| Sample | % TUNEL positive cells |
| --- | --- |
| Attached retina (right eye) | 1.3% TUNEL positive |
| Detached retina (left eye) | 21.6% TUNEL positive |
| Detached retina (left eye) plus DMSO only | 33.3% TUNEL positive |
| Detached retina (left eye) plus caspase 9 inhibitor | 4.6% TUNEL positive |

The results in Table 1 demonstrate that in the eyes with the detached retinas, the administration of the caspase 9 inhibitor significantly reduced the percentage of apoptotic cells and, therefore, preserved photoreceptor viability following retinal detachment.

INCORPORATION BY REFERENCE

The entire disclosure of each of the patent and non-patent documents disclosed herein is expressly incorporated herein by reference for all purposes.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A method of preserving the viability of photoreceptor cells disposed within a retina of a mammalian eye following retinal detachment, the method comprising:

administering to a mammal's retina, the mammal having an eye in which a region of the retina has been detached, an amount of an apoptosis inhibitor sufficient to preserve the viability of photoreceptor cells disposed within the region of the detached retina, wherein the apoptosis inhibitor comprises an anti-FAS-ligand antibody or an anti-FAS-receptor antibody.

2. The method of claim 1, wherein the apoptosis inhibitor is administered to the mammal prior to reattachment of the region of detached retina.

3. The method of claim 1 or 2, wherein the apoptosis inhibitor is administered to the mammal after reattachment of the region of detached retina.

4. The method of claim 1, wherein a plurality of apoptosis inhibitors are administered to the mammal.

5. The method of claim 1, wherein at least one apoptosis inhibitor is administered by intraocular, intravitreal, or transcleral administration.

6. The method of claim 1, wherein the apoptosis inhibitor reduces the number of photoreceptor cells in the region that die following retinal detachment relative to the number of photoreceptor cells that die in the absence of the apoptosis inhibitor.

7. The method of claim 1, wherein the photoreceptor cells comprise rods and cones.

8. The method of claim 1, wherein the retinal detachment occurs as a result of a retinal tear, retinoblastoma, melanoma, diabetic retinopathy, uveitis, choroidal neovascularization, retinal ischemia, pathologic myopia, or trauma.

9. The method of claim 1, wherein the apoptosis inhibitor is an anti-FAS-ligand antibody.

10. The method of claim 1, wherein the apoptosis inhibitor is an anti-FAS-receptor antibody.

* * * * *